United States Patent [19]

Krantz et al.

[11] Patent Number: 4,745,116

[45] Date of Patent: * May 17, 1988

[54] 2-OXY-4H-3,1-BENZOXAZIN-4-ONES AND RELATED COMPOUNDS AND PHARMACEUTICAL USE

[75] Inventors: Alexander Krantz, Toronto; Robin Spencer, Mississauga; Tim Tam, Mississauga; Teng J. Liak, Mississauga, all of Canada

[73] Assignee: Syntex (U.S.A.) Inc., Palo Alto, Calif.

[*] Notice: The portion of the term of this patent subsequent to May 12, 2004 has been disclaimed.

[21] Appl. No.: 945,751

[22] Filed: Dec. 23, 1986

Related U.S. Application Data

[63] Continuation-in-part of Ser. No. 748,631, Jun. 25, 1985, Pat. No. 4,665,070.

[51] Int. Cl.$^4$ .................. A61K 31/535; C07D 265/36
[52] U.S. Cl. ...................................... 514/230.5; 544/93
[58] Field of Search ................ 544/93; 514/232, 234, 514/235, 236, 237, 239

[56] References Cited

U.S. PATENT DOCUMENTS 4,665,070 5/1987 Krantz et al. .................. 514/232

FOREIGN PATENT DOCUMENTS 2241012 3/1973 Fed. Rep. of Germany .

OTHER PUBLICATIONS

Kantlehner et al., Liebigs Ann. Chem., (1982), pp. 507-529.
Dunn et al., J. Het. Chem., vol. 20, (1983), pp. 779-780.
Hedstrom et al., Biochemistry, vol. 23, (1984), pp. 1753-1759.

Primary Examiner—Richard L. Raymond
Attorney, Agent, or Firm—Carol J. Roth; Tom M. Moran

[57] ABSTRACT

2-Oxy-4H-3,1-benzoxazin-4-ones, useful as serine protease inhibitors, represented by the formula:

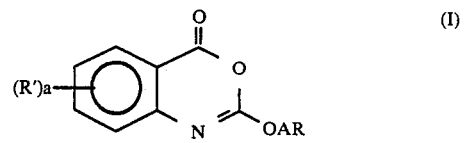

and the pharmaceutically acceptable acid addition salts thereof, wherein:

a is an integer of 1 to 4;

A is a bond, or alkylene having one to eight carbon atoms;

R is hydrogen, phenyl, imidazolyl or cycloalkyl having three to six carbon atoms, wherein the phenyl, imidazolyl or cycloalkyl ring is optionally substituted with 1 to 3 substituents independently selected from the group consisting of lower alkyl having one to four carbon atoms, lower alkoxy having one to four carbon atoms, $-N(R^1)_2$, $-NO_2$, halo or lower alkylthio having one to four carbon atoms, and, each R' is independently selected from the group consisting of hydroxy, benzyloxy, lower alkyl having one to six atoms, lower alkenyl having two to six carbon atoms, lower alkoxy having one to six carbon atoms, lower alkylthio or halo-lower alkyl having one to six carbon atoms, halo, $-NO_2$, $-N(R^1)_2$, $-NR^1CO_2R^2$, $-NR^1COR^2$, and $-NR^1C(O)N(R^1)_2$, in which each $R^1$ is independently hydrogen or lower alkyl having one to four carbon atoms, or together form a piperidine or a piperazine ring optionally substituted at the ring nitrogen by lower alkyl having one to four carbon atoms or $-CH_2CH_2OH$;

each $R^2$ is independently lower alkyl having one to four carbon atoms,

A is an alkylene group if R is hydrogen, or a pharmaceutically acceptable acid addition salt thereof.

38 Claims, No Drawings

2-OXY-4H-3,1-BENZOXAZIN-4-ONES AND RELATED COMPOUNDS AND PHARMACEUTICAL USE

RELATED APPLICATIONS

This application is a continuation-in-part of U.S. patent application Ser. No. 748,631, filed June 25, 1985, and owned by the assignee of the present invention, now U.S. Pat. No. 4,665,070. The parent application is hereby fully incorporated by reference into the instant application, as though set forth herein.

BACKGROUND OF THE INVENTION

1. Field of the Invention

This invention relates to (i) 2-oxy-4H-3,1-benzoxazin-4-ones and the pharmaceutically acceptable acid addition salts thereof; (ii) the use of these compounds as serine protease inhibitors in humans and animals; (iii) pharmaceutical compositions comprising a compound of this invention and at least one pharmaceutical excipient; and (iv) processes for preparing the compounds of this invention.

2. Related Art

The compounds of this invention are 2-oxy substituted derivatives of 4H-3,1-benzoxazinones having the following structure:

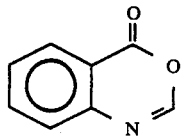

2-Ethoxy-4H-3,1-benzoxazin-4-one is disclosed in British Patent Specification No. 1,389,128 and in the corresponding German Offenlegungschrift No. 2241012. A few 4H-3,1-benzoxazin-4-ones are known to possess enzyme-inhibitory activity. Teshima et al. have disclosed various 2-alkyl-4H-3,1-benzoxazin-4-ones reported to be active as enzyme inhibitors (*J. Biol. Chem.*, 257, 5085–5091, 1982). 4H-3,1-benzoxazin-2,4-dione has been disclosed as having enzyme inhibitory activity (Moorman, A. R., and Abeles, R. H. *J. Amer. Chem. Soc.* 104, 6785–6786, 1982). 2-Ethoxy-4H-3,1-benzoxazinone and 2-(trifluoromethyl)-4H-3,1-benzoxazinone inhibit chymotrypsin (Hedstrom et al, *Biochemistry* 23, 1753–1759, 1984).

SUMMARY

We have discovered that the class of 2-oxy-4H-3,1-benzoxazin-4-ones of Formula I, as shown below:

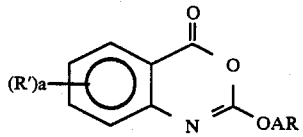

and described and claimed herein, are biologically active as inhibitors of enzymes, and in particular are inhibitors of serine proteases. Within this class, several groups of compounds are novel and preferred. Accordingly, the invention described and claimed herein contains the following aspects:

1. Novel compounds of Formula I wherein:
A is an integer of 1 to 4;
A is alkylene having one to eight carbon atoms;
R is hydrogen; and
each R' is independently selected from the group consisting of hydroxy, benzyloxy, lower alkyl having one to six carbon atoms, lower alkenyl having two to six carbon atoms, lower alkoxy having one to six carbon atoms, halo-lower alkyl having one to six carbon atoms, lower alkylthio having one to six carbon atoms, halo, —NO$_2$, —N(R$^1$)$_2$, —NR$^1$CO$_2$R$^2$, —NR$^1$COR$^2$, and —NR$^1$C(O)N(R$^1$)$_2$,
in which
each R$^1$ is independently hydrogen or lower alkyl having one to four carbon atoms, or together form a piperidine or piperazine ring optionally substituted at the ring nitrogen by lower alkyl having one to four carbon atoms or —CH$_2$CH$_2$OH, and
each R$^2$ is independently lower alkyl having one to four carbon atoms,
or a pharmaceutically acceptable acid addition salt thereof.

2. Novel compounds of Formula A:

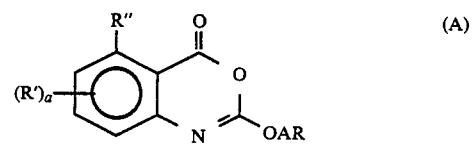

wherein:
a is an integer of 0 to 3;
A is a bond, or alkylene having one to eight carbon atoms;
R is hydrogen, imidazolyl, phenyl, or cycloalkyl having three to six carbon atoms, wherein the phenyl, imidazolyl or cycloalkyl ring is optionally substituted with 1 to 3 substituents independently selected from the group consisting of lower alkyl having one to four carbon atoms, lower alkoxy having one to four carbon atoms, —N(R$^1$)$_2$, —NO$_2$, halo, and lower alkylthio having one to four carbon atoms; and
each R' and R" are independently selected from the group consisting of hydroxy, benzyloxy, lower alkyl having one to six carbon atoms, lower alkenyl having two to six carbon atoms, lower alkoxy having one to six carbon atoms, lower alkylthio having one to six carbon atoms, halo, halo-lower alkyl having one to six carbon atoms, —NO$_2$, —N(R$^1$)$_2$, —NR$^1$CO$_2$R$^2$, —NR$^1$COR$^2$, and —NR$^1$C(OR)N(R$^1$)$_2$,
in which
each R$^1$ is independently hydrogen or lower alkyl having one to six carbon atoms, or together form a piperidine or piperazine ring optionally substituted at the ring nitrogen with lower alkyl having one to four carbon atoms or —CH$_2$CH$_2$OH;
each R$^2$ is independently lower alkyl having one to four carbon atoms, and
A is alkylene if R is hydrogen,
or a pharmaceutically acceptable acid addition salt thereof.

3. Pharmaceutical compositions which comprise a therapeutically effective amount of a compound of Formula I or A chosen from among those described in Groups 1 and 2 above, or a pharmaceutically acceptable acid addition salt thereof, in admixture with at least one pharmaceutically acceptable excipient.

4. Methods of inhibiting serine proteases in humans and animals which comprise administering to a subject in need of such treatment a therapeutically effective amount of a compound of Formula I or A chosen from among those described in Groups 1 and 2, above.

5. A method of inhibiting serine proteases in humans and animals which method comprises administering to a subject in need of such treatment a therapeutically effective amount of a compound of the formula:

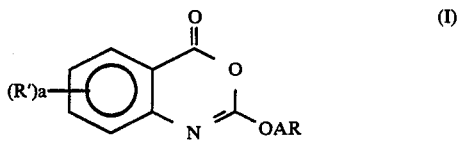

wherein:

a is an integer of 1 to 4;

A is a bond, or alkylene having one to eight carbon atoms;

R is hydrogen, phenyl, imidazolyl or cycloalkyl having three to six carbon atoms, wherein the phenyl, imidazolyl, or cycloalkyl ring is optionally substituted with 1–3 substituents independently selected from the group consisting of lower alkyl having one to four carbon atoms, lower alkoxy having one to four carbon atoms, $-N(R^1)_2$, $-NO_2$, halo, and lower alkylthio having one to four carbon atoms; and each R' is independently selected from the group consisting of hydroxy, benzyloxy, lower alkyl having one to six carbon atoms, lower alkenyl having two to six carbon atoms, halo, lower alkoxy having one to six carbon atoms, lower alkylthio or halo-lower alkyl having one to six carbon atoms, $-NO_2$, $-N(R^1)_2$, $-NR^1CO_2R^2$, $-NR^1COR^2$, and $-NR^1C(O)N(R^1)_2$, in which each $R^1$ is independently hydrogen or lower alkyl having one to four carbon atoms, or together form a piperidine or piperazine ring optionally substituted at the ring nitrogen with lower alkyl having one to four carbon atoms or $-CH_2CH_2OH$;

each $R^2$ is independently lower alkyl having one to four carbon atoms, and

A is alkylene if R is hydrogen, or a pharmaceutically acceptable acid addition salt thereof.

DETAILED DESCRIPTION OF THE INVENTION

As used herein:

"Alkylene" means a branched or unbranched saturated hydrocarbon bridging group having one to eight carbon atoms, including but not limited to, methylene, ethylene, propylene, isopropylene, n-propylene, butylene, sec-butylene, isobutylene, n-pentylene, hexylene, octylene, and the like.

"Lower alkyl" means a branched or unbranched saturated hydrocarbon chain having, unless otherwise noted, one to six carbon atoms, including but not limited to methyl, ethyl, propyl, isopropyl, n-propyl, butyl, sec-butyl, isobutyl, n-pentyl, hexyl, octyl and the like. Lower alkyl groups may be limited to fewer than six carbon atoms when specifically designated, e.g. "$R^2$ is lower alkyl having one to four carbon atoms."

"Lower alkenyl" means a branched or unbranched unsaturated hydrocarbon chain of 2 to 6 carbon atoms, including but not limited to vinyl, allyl, 1-propenyl, isopropenyl, 1-butenyl, 2-butenyl, isobutenyl, 1,3-butadienyl, 1-pentenyl, 2-pentenyl, isoprenyl, 1-hexenyl, 2-hexenyl, 3-hexenyl, cis-2-butenyl, trans-2-butenyl, cis-2-pentenyl, trans-2-pentenyl, 3-methyl-1-butenyl, 2-methyl-2-butenyl and 2,3-dimethyl-2-butenyl.

"Lower alkoxy" means the group —OR wherein R is lower alkyl as herein defined.

"Lower alkylthio" means the group —SR wherein R is lower alkyl as herein defined.

"Halo" refers to chloro, bromo and iodo.

"Halo-lower alkyl" means the group —R-halo in which R is lower alkyl, and both lower alkyl and halo have the definitions given herein. The alkyl group may bear one or two halo substituents; examples include but are not limited to bromomethyl, dibromomethyl, chloroethyl, dichloroethyl, and the like.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethane sulfonic acid, p-toluenesulfonic acid, ascorbic acid, salicylic acid and the like.

"Optional" or "optionally" means that the subsequently described event or circumstances may or may not occur, and that the description includes instances where said event or circumstance occurs and instances in which it does not. For example, "phenyl . . . optionally substituted" means that the phenyl may or may not be substituted and that the description includes both unsubstituted phenyl and phenyl wherein there is substitution.

Certain of the compounds of the invention have chiral centers and exist as optical antipodes. The invention described and claimed herein includes each of the individual enantiomers as well as their racemic modifications and the racemic mixture.

The compounds of this invention are named as 2-oxy-4H-3,1-benzoxazin-4-ones using the numbering system set forth below.

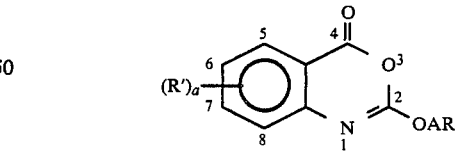

For example, the compound of Formula I where AR is isopropyl, a is 1 and R' is methyl in the 5-position is named 2-isopropyloxy-5-methyl-4H-3,1-benzoxazin-4-one.

The compound where AR is phenethyl, a is 2 and both R's are amino in the 5- and 7-positions is named 2-(phenethyloxy)-5,7-di-amino-4H-3,1-benzoxazin-4-one.

The compound of Formula I where AR is cyclohexyl, and a is zero is named 2-cyclohexyloxy-4H-3,1-benzoxazin-4-one.

The compound of Formula I where AR is n-butyl, a is 1 and R' is methylthio in the 5-position is named 2-n-butoxy-5-methylthio-4H-3,1-benzoxazin-4-one.

PREFERRED EMBODIMENTS

Within the several aspects of this invention which are set forth as Groups 1 to 4 in the Summary of the Invention, certain subgroups are preferred. The metes and bounds of these subgroups and their relative degrees of preference are described below.

Within each of the groups of compounds defined as Groups 1 to 4, preferred subgroups are compounds of Formula A in which a is at least one. Among these, preferred classes encompass compounds in which the R's are in the 7- and/or 8-positions. Within these classes, preferred subclasses include compounds of Formula A in which an R' is in the 7-position and compounds of Formula A in which a first R' is in the 7-position and a second R' is in the 8-position.

Preferred R' substituents at the 8-position are lower alkyl having one to six carbon atoms, lower alkenyl having two to six carbon atoms and lower alkoxy having one to six carbon atoms. Especially preferred R' substituents at the 8-position are lower alkyl having one to six carbon atoms, particularly one to three carbon atoms, and most particularly methyl or ethyl. Preferred R' substituents at the 7-position are hydroxy, benzyloxy, lower alkoxy having one to six carbon atoms, $-NO_2$ and $-N(R^1)_2$. Especially preferred R' substituents at the 7-position are hydroxy and $-N(R^1)_2$, especially where R'' is methyl or ethyl.

Additionally, certain subgroups within each individual Group have preference. Among the compounds of Formula I as set forth in Group 1, a preferred subgroup is those compounds in which A is a bond, or alkylene having one to four carbon atoms, especially a bond or methylene. Among the compounds of Formula I defined by Group 2, a preferred subgroup are those compounds in which A is lower alkylene having one to four carbon atoms, particularly methylene and ethylene. Among the compounds of Formula I as set forth in Group 3, a preferred subgroup encompasses compounds in which A is alkylene having five to eight carbon atoms. Among the compounds of Formula A as defined in Group 4, a preferred subgroup consists of compounds in which a is one or two and A is lower alkylene having one to four carbon atoms, particularly methylene and ethylene.

At the present time, the most preferred compounds of this invention are:

7-amino-2-ethoxy-5,8-dimethyl-4H-3,1-benzoxazin-4-one;

7-amino-2-ethoxy-5-ethyl-4H-3,1-benzoxazin-4-one;

7-amino-2-ethoxy-8-ethyl-5-methyl-4H-3,1-benzoxazin-4-one;

2-ethoxy-7-hydroxy-5-methyl-4H-3,1-benzoxazin-4-one;

7-hydroxy-2-isopropoxy-5-methyl-4H-3,1-benzoxazin-4-one;

5-ethyl-7-hydroxy-2-isopropoxy-4H-3,1-benzoxazin-4-one;

2-ethoxy-7-methoxy-5-methyl-4H-3,1-benzoxazin-4-one;

7-benzyloxy-2-ethoxy-5-methyl-4H-3,1-benzoxazin-4-one.

METHODS OF PREPARATION

In this section the remainder of the specification, the compounds of the invention which are referred to in the Summary of the Invention and in the Claims as compounds of Formula I and compounds of Formula A will be referred to collectively as compounds of Formula I, and further defined as compounds of Formula IA, IB, IC, etc.

A. Compounds of Formula I in Which R' is Lower Alkyl, Lower Alkoxy, Lower Alkylthio, Halo, $-NO_2$ or an Amine Other than $NH_2$ (Compounds of Formula IA)

The compounds of Formula I in which each R' substituent is lower alkyl, lower alkoxy, lower alkylthio, halo, $-NO_2$ or an amine other than $-NH_2$, (hereinafter defined as compounds of Formula IA), can be prepared by the general procedure set forth in Reaction Scheme I, below.

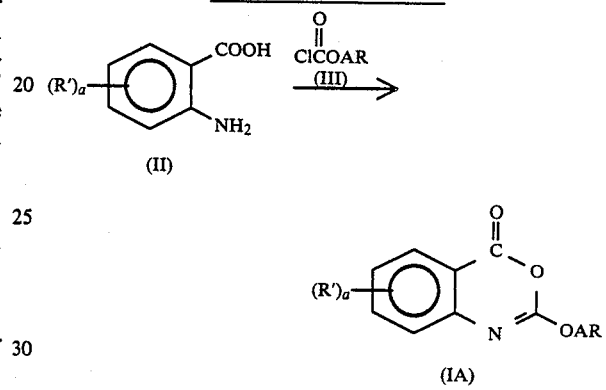

REACTION SCHEME I

As outlined in Reaction Scheme I, the compounds of Formula IA are prepared by cyclization of the corresponding appropriately substituted or unsubstituted anthranilic acid. Cyclization is preferably achieved by reaction of the chosen anthranilic acid with about 3 to about 5, preferably about 4 equivalents of the desired phenyl-, cycloalkyl- or alkyl chloroformates of the formula ClCOOAR, wherein A and R are defined as hereinabove. The reaction takes place in a basic organic solvent such as triethylamine, or, preferably, pyridine, and is carried out at room temperature over a period of about 0.5 to about 5 hours, preferably about 1 to about 3 hours. The final product, a compound of Formula IA, is then isolated by conventional means.

Isolation and purification of the final compounds and intermediates described herein can be effected, if desired, by any suitable separation or purification procedure such as, for example, filtration, extraction, crystallization, column chromatography, thin-layer chromatography, thick layer chromatography, or a combination of these procedures. Specific illustrations of suitable separation and isolation procedures can be had by reference to the examples hereinbelow. However, other equivalent separation or isolation procedures could, of course, also be used.

Unsubstituted anthranilic acid is readily commercially available. The substituted anthranilic acids (Formula II) used in preparing the compounds of this invention are either commercially available, or can be prepared by methods well known in the art. The commercially available anthranilic acids include, but are not limited to, 3-methyl-anthranilic acid, 4-methyl anthranilic acid, 5-methyl-anthranilic acid, 6-methyl-anthranilic acid, 5-iodo-anthranilic acid, 4-nitro-anthranilic acid, and 4,5-dimethoxy-anthranilic acid. A list of commercially available anthranilic acids is available in *Chem. Sources*-U.S.A., 24th Ed., 1983, Directories Publishing Company, Inc., Ormond Beach, Fla. Appropriately substituted anthranilic acids which are not commercially available can be readily prepared by methods known in the art. Suitable methods include those of B. R. Baker, et al., *J. Org. Chem.*, 17, 141, (1952) and of L. A. Paquette, et al., *J. Am. Chem. Soc.* 99, 3734, (1981). The former method involves the preparation of an isatin from a substituted aniline derivative. Subsequent oxidation of the isatin gives the anthranilic acid. The latter procedure employs the reduction of the corresponding aromatic nitro-derivative to the anthranilic acid. These methods are further illustrated in Preparation I, below.

The phenyl-, cycloalkyl- and alkyl chloroformates of Formula III are either commercially available, or can be prepared by methods well known or readily available in the chemical literature. Commercially available chloroformates include, but are not limited to benzyl chloroformate, methyl chloroformate, ethyl chloroformate, n-butyl chloroformate, isobutyl chloroformate. Suitable chloroformates which are not commercially available can be prepared by known methods. Preparative methods include those of D. H. R. Barton et al., *J. Chem Soc.* 18 55–1857 (1968) and K. Kurita et al., *J. Org Chem.* 41, 2070–2071, (1976). The former method involves treatment of an appropriate alcohol with phosgene in an inert solvent such as anhydrous ether. Further description of this method is provided in Preparation II, below. The latter procedure involves the reaction of an appropriate alcohol with trichloromethyl chloroformate (diphosgene) in dry dioxane at refluxing temperature.

B. Compounds of Formula I in Which an R' is $NH_2$ (Compounds of Formula IB)

Compounds of Formula I in which one of the R' substituents is $NH_2$ (hereinafter referred to as compounds of Formula IB) can be prepared by the procedure set forth in Reaction Scheme II, below.

REACTION SCHEME II

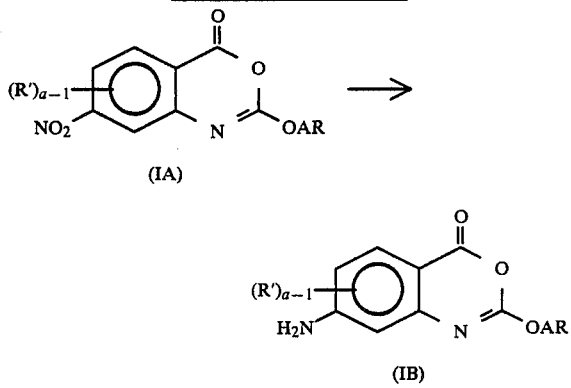

As shown above, a nitro-substituted 2-oxy-4H-3,1-benzoxazin-4-one of Formula IA is reduced to the corresponding amino-substituted compound of Formula I by transfer hydrogenation. The reaction takes place in benzene or THF in the presence of 10% Pd-C as catalyst and cyclohexene as hydrogen donor and is carried out at reflux temperature over about one to five, preferably about three hours. The final product, a compound of Formula IB, is then isolated by conventional means.

The nitro-substituted benzoxazinone of Formula IA may be commercially obtained, or is prepared according to the procedure set forth above in Section A.

C. Compounds in Which an R' is $-NR^1COR^2$ (Compounds of Formula IC)

Compounds of the invention in which one of the R' substituents is an amine of the formula $-NR^1COR^2$, (hereinafter referred to as compounds of Formula IC) can be prepared from the corresponding amino-substituted compound of Formula IB, as shown in Reaction Scheme III.

REACTION SCHEME III

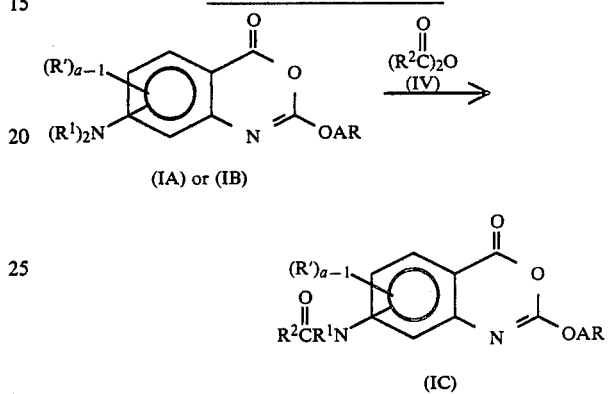

The amino-substituted compound of Formula IA or IB, prepared as described in section A or B, above, is reacted with about 1 to 3 equivalents of an appropriate acid anhydride of Formula IV, with or without the presence of an inert organic solvent such as dichloromethane or tetrahydrofuran. The reaction takes place at room temperature over a period of about 15 min to about 3 hrs, usually about 1 hour, and the final product, a compound of Formula IC, is then isolated by conventional means.

The acid anhydrides (Formula IV) used in preparing the compounds of Formula IC are either commercially available or can be prepared by methods well known in the art. The commerially available acid anhydrides include, but are not limited to, acetic anhydride, propionic anhydride, and butyric anhydride. A list of commercially available acid anhydrides is available in *Chem. Sources*-U.S.A., 24th Ed., 1983, Directories Publishing Company, Inc., Ormond Beach, Fla. Acid anhydrides which are not commercially available can be readily prepared by methods known in the art. Suitable methods include the direct removal of water from acids to form acid anhydride and from acid chlorides and alkali salts of carboxylic acids by mixing the reactants and distilling off the anhydride formed as described in *Preparative Organic Chemistry*, edited by G. Hilgetag and A. Martini, page 387–390, John Wiley & Sons, New York-London-Sydney-Toronto (1972), and further illustrated in Preparation III, below.

D. Compounds in Which an R' is $-NR^1CO_2R^2$ (Compounds of Formula ID)

Compounds of the invention which bear an R' substituent of the formula $-NR^1CO_2R^2$ can be prepared by the procedure set forth in Section A, above, or from the corresponding amino-substituted compound of Formula IA or IB, as shown below.

REACTION SCHEME IV

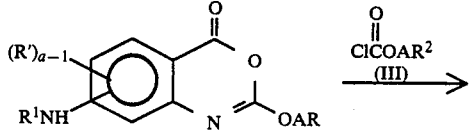

REACTION SCHEME V

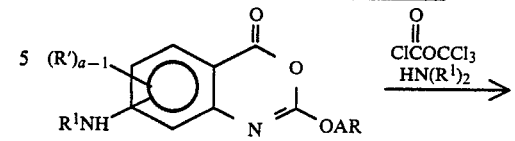

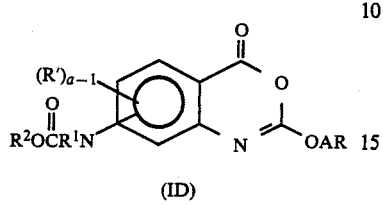

In carrying out the above conversion, the appropriate compound of Formula IA or IB (prepared as described in Sections A and B, above) bearing an R¹NH substituted as shown, is reacted with about one to three equivalents, preferably about 1.5 equivalents, of an appropriately chosen phenoxy-, cycloalkoxy- or alkoxy chloroformate of Formula III. (The commercial availability and methods of preparing the various compounds of Formula III used in making the compounds of this invention are discussed in detail in Section A, hereinabove.) The reaction takes place in an inert solvent such as dichloromethane or tetrahydrofuran in the presence of a tertiary amine such as triethylamine or, preferably, pyridine, at room temperature over a period of about one to about three, usually about two, hours. The final product, a compound of Formla ID, is then isolated by conventional means.

E. Compounds in Which an R' is —NR¹C(O)N(R¹)₂ (Formula IE)

Compounds of the invention which bear an R' substituent of the formula —NR¹CON(R¹)₂ (hereinafter referred to as compounds of Formula IE) can be prepared from the corresponding amino-substituted compounds of Formula IA and IB as shown below in Reaction Scheme V.

The amino-substituted compound of Formula IA or IB is reacted in an inert solvent such as benzene or tetrahydrofuran with about 0.5 to 1 preferably 0.75, equivalent of trichloromethyl chloroformate, for a period of about 15 to 60 minutes, preferably about 30 minutes. Without isolation, the resulting carbamyl chloride derivative is then treated with about 5 to 10, preferably about 7.5 equivalents of pyridine and about 1 to 3, preferably about 2 equivalents of an appropriate primary or secondary alkyl amine for a period of about 15 to 60, usually about 30 minutes. The final product, a compound of Formula IE, is then isolated by conventional means.

F. Compounds in which an R' is Halo-Lower Alkyl (Formula IF)

Compounds of the Formula I which bear an R' substituent in which R' is lower alkyl can be mono- or di-halogenated at a benzylic position with an N-halosuccinimide such as N-bromosuccinimide, and AIBN (2,2'-azobis-isobutyronitrile) to give either the monohalo compound of Formula (IF₁) or the di-halo compound of Formula (IF₂). Normally, only a catalytic amount of AIBN is used. This procedure is shown in Reaction Scheme VI, below, in which N-bromosuccinimide is used as an example. N-chlorosuccinamide or N-iodosuccinimide can also be used.

REACTION SCHEME VI

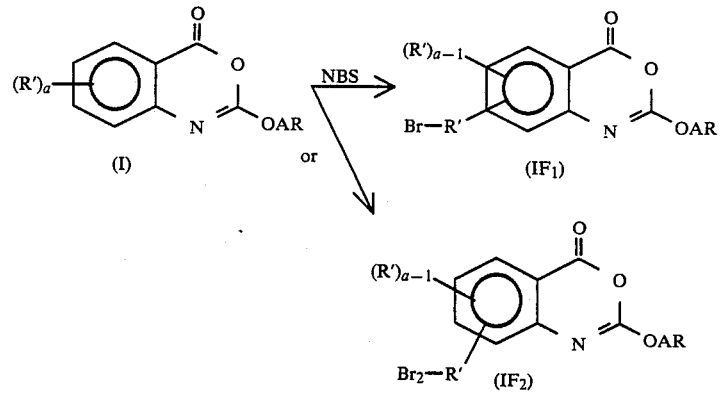

The halogenation reaction is carried out in carbon tetrachloride at reflux temperature for 2 to 4 hours, and the product is isolated by conventional means. When, for example, one equivalent of N-bromosuccinimide is used, the monobromo compound of Formula IF₁ is the major product; likewise, when two equivalents of N-bromosuccinimide are used, the dibromo compound of Formula IF₂ is the major product.

G. Compounds in Which an R' is Lower Alkenyl or Lower Alkyl

Compounds of Formula I in which an R' is lower alkyenyl or lower alkyl can be prepared from the corresponding compounds of Formula IF₁ and IG₂, as shown in Reaction Scheme VII. Compounds of Formula I in which an R' is lower alkyl can also be prepared by the method described in Section A, above.

from about −40° C. to −60° C., preferably −50° C., to form the Wittig ylid. Subsequent quenching with an alkyl aldehyde gives the compound of Formula IG₃. The reaction is normally carried out in dry tetrahydrofuran; and the product is recovered by conventional means. The compound of Formula IG₃ represents a mixture of both (E) and (Z) enantiomers.

H. Compounds in which R is Imidazolyl (Formula IH)

Compounds of Formula I in which R is imidazolyl (compounds of Formula IH) can be prepared by the method shown in Reaction Scheme VIII, below:

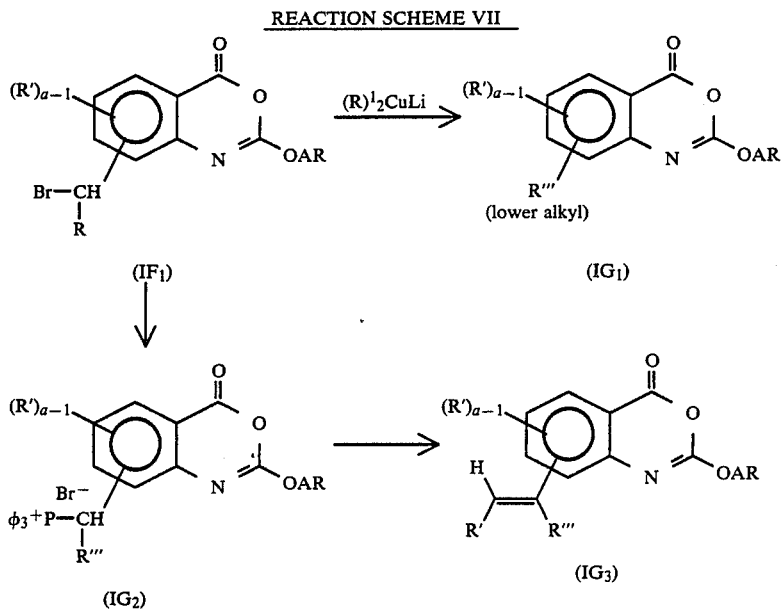

REACTION SCHEME VII

In Formulas IF₁, IG₁ and IG₂, R' is hydrogen or lower alkyl having one to six carbon atoms. In Formula IG₃, R' is the remaining saturated portion of the alkene substituent. For illustrative purposes the double bond is depicted at carbons 2-3; however, other straight and branched chain lower alkene substituents can be obtained by the method shown in Reaction Scheme VII from the appropriate corresponding triphenylphosphine intermediate of Formula IG₂.

As shown in Reaction Scheme VII, a compound of Formula IF₁ reacts with lithium dialkyl cuprate at low temperature to give the compound of Formula IG₁. The reaction is normally carried out in an ethereal solvent, preferably anhydrous diethyl ether, at about −25° C. to −78° C., preferably about −40° C. The displacement of benzyl bromide with lithium dialkyl cuprate is known in the art, (see *Organic Reactions*, Vol. 13, pp. 252 and 401, (John Wiley & Sons) and G. H. Posner, *Substitution Reactions using Organocopper Reagents;* John Wiley & Sons (1980)) and is further illustrated in Example VII, below.

The monobromo compound of Formula IF₁ can be converted to the Wittig salt of Formula IG₂ by reacting with triphenylphosphine in toluene. The reaction is preferably carried out between 60° C. to 70° C., preferably 65° C., for a period of about 4 to 6, preferably about 5 hours.

A compound of Formula IG₂ reacts with one equivalent of DBU (1,8-diazabicyclo[5,4,0]-undec-7-ene) at

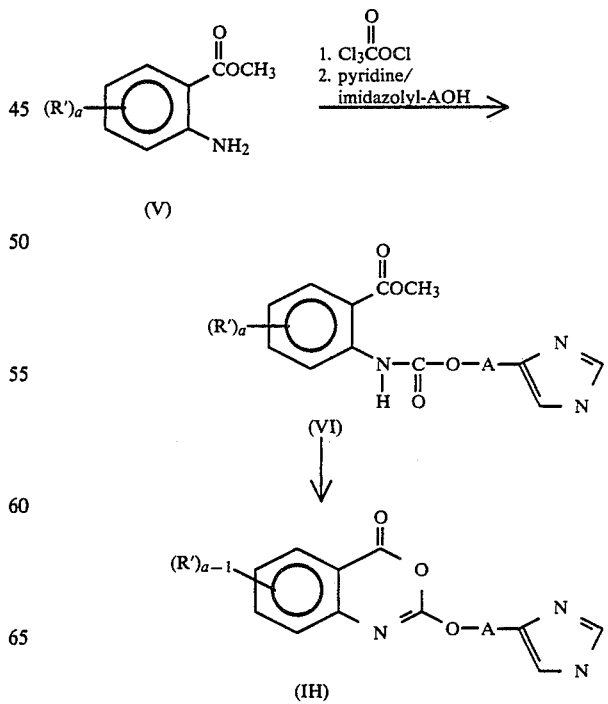

As shown in Reaction Scheme VIII, the compounds of Formula VI are prepared from the corresponding methyl anthranilate derivative of Formula V. Methyl anthranilate, as well as variously substituted methyl 2-amino benzoates (methyl anthranilates) are commercially available, or can be prepared by treating the corresponding anthranilic acid with diazomethane in an inert organic solvent such as tetrahydrofuran or preferably ether at about 0° C., a method that is standard for the formation of methyl esters. Alternatively, variously substituted methyl 2-amino benzoates can be prepared by treating the corresponding isatoic anhydride with methanol in the presence of base such as sodium mehtoxide or dimethylaminopyridine, preferably dimethylaminopyridine, according to the literature methods such as that reported by M. C. Venuti, *Synthesis*, 266 (1982), R. P. Straiger and E. B. Miller, *J. Org. Chem.*, 24, 1214 (1959).

pound of Formula IH is obtained by base hydrolysis of the compound of Formula VI to the corresponding carboxylic acid, followed by cyclization with DCC or EDC in an inert solvent such as dichloromethane or tetrahydrofuran. The cyclization reaction takes place at room temperature over a period of about 1 to 3 hours, and the final product is then isolated by conventional means.

I. Compounds of Formula I in which an R' is Alkyl at the 5-Position and a Second R' is Nitro or Amino at the 7-Position (Formulas IA and IB)

Compounds of Formula I which bear a lower alkyl R' substituent at the 5-position and a nitro or amino R' substituent at the 7-position (compounds of Formulas IA and IB) can be prepared by the procedures set forth in Reaction Schemes I and II, or alternatively, by the procedure illustrated below in Reaction Scheme IX.

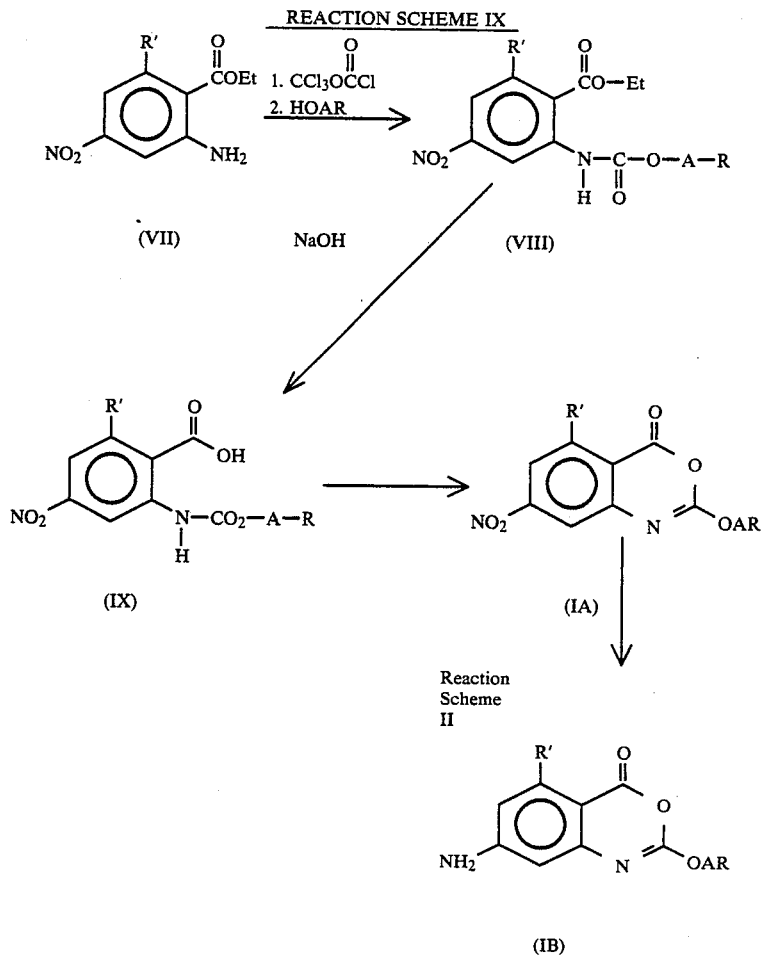

The corresponding unsubstituted or appropriately substituted anthranilate of Formula V is treated with about 0.5 to 1 equivalent of trichloromethyl chloroformate in tetrahydrofuran at room temperature for a period of about 1 to 2, preferably about 1.5 hours; the resulting carbamyl chloride derivative is then refluxed with about 1 to 2 equivalents of 4(N-triphenylmethyl-)imidazolylmethanol, or another appropriate imidazolyl alcohol, in the presence of 5 to 10 equivalents of a tertiary amine, preferably triethylamine, for a period of about 0.5 to 2 hours. The product, a compound of Formula VI, is isolated by conventional means. The com- As shown in Reaction Scheme IX, the appropriately substituted ethyl anthranilate of Formula VII is converted to the carbamoyl chloride derivative by treatment with about 0.5 to 1, preferably about 0.75 equivalents of trichloromethyl chloroformate in ethyl acetate at room temperature for a period of about 2 to 3, preferably 2, hours. The resulting carbamoyl chloride derivative is then quenched with about a five fold excess of an appropriate alcohol of the formula HOAR (in which A and R have the difinitions given herein), and a base such as pyridine or triethylamine. The product of Formula VIII is isolated by conventional means. Base hydolysis of the compound of Formula VIII is then carried out in about a 1:1 mixture of aqueous sodium hydroxide and 1,2-dimethoxyethane to give the carboxylic acid of Formula IX. The acid of Formula IX is then cyclized with DCC or EDC in an inert organic solvent to give the final product of Formula IA, which is then isolated by conventional means.

The amino substituted compound of Formula IB can then be obtained form the corresponding nitro substituted compound of Formula IA by the procedure outlined in Reaction Scheme II.

Preparation of the ethyl anthranilate starting materials of Formula VII can be accomplished by the method illustrated in Reaction Scheme X, as follows:

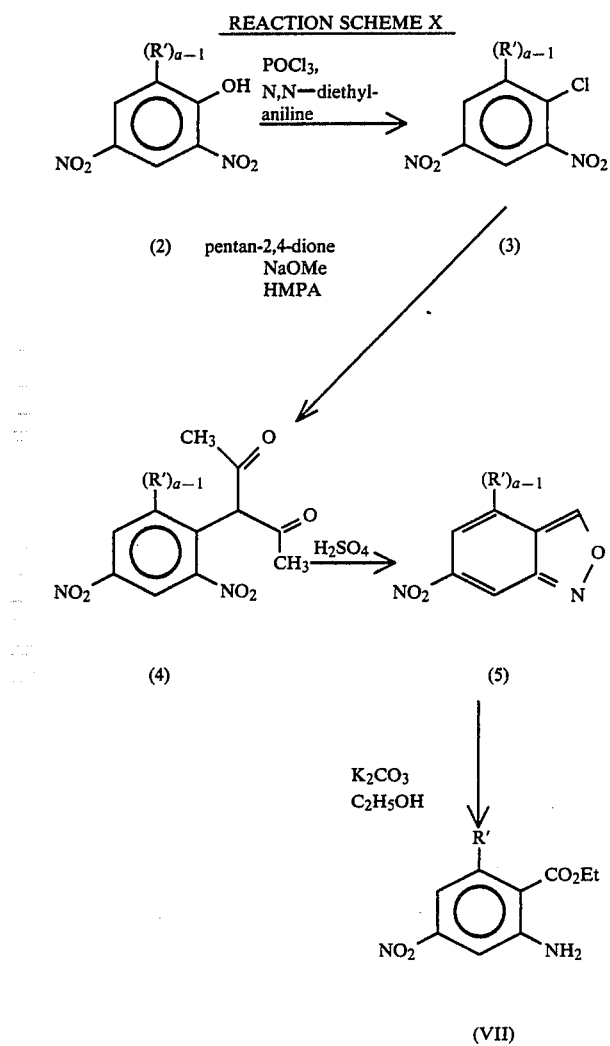

As shown in Reaction Scheme X, above, the di-nitro phenol derivative of Formula 2, which is either commercially available of readily prepared by standard known methods such as those illustrated in Preparation IV, Paragraph A, herein, is converted to the corresponding chloro-compound of Formula 3 according to the procedure described by B. Boothroyd and E. R. Clark, *J. Chem. Soc.*, p. 1504, London (1953). Details of this reaction may also be had by reference to Preparation IV, Paragraph B, below. The compound of Formula 3 is then reacted at room temperature with about a 10 fold excess of pentan-2,4-dione and about a 3–4 fold excess of sodium methoxide in the presence of HMPA as solvent, to give the (2-alkyl-4,6-dinitrophenyl)-diacetylmethane of Formula 4. The compound of Formula 4 is then cyclized in concentrated sulphuric acid at about 100°–120° C., preferably about 110° C. for a period of about 1 to 5, preferably about 3 hours, to give the 4-alkyl-6nitro anthranil of Formula 5. Details of this procedure may be had by reference to the method described by I. R. Gambir and S. S. Joshi in the *Indian Chem. Soc.* Journal, V.41, pp. 43–46 (1964), which is specifically illustrated in Preparation IV, Paragraph C, herein. Subsequent ring opening by treating the anthril of Formula 5 with potassium carbonate and ethanol at reflux temperature gives the ethyl 4-nitro-6-alkyl-2-amino benzoate of Formula VII.

J. Compound of Formula A in which a R' is hydroxy, lower alkoxy, or benzyloxy at the 7-position (Formula XF, XG, and X)

Compounds of Formula A which bear a hydroxy, lower alkoxy, or benzylxoy R' substituent at the 7-position (compounds of Formula XF, XG, and X) can be prepared by the procedures set forth in Reaction Scheme XI, below:

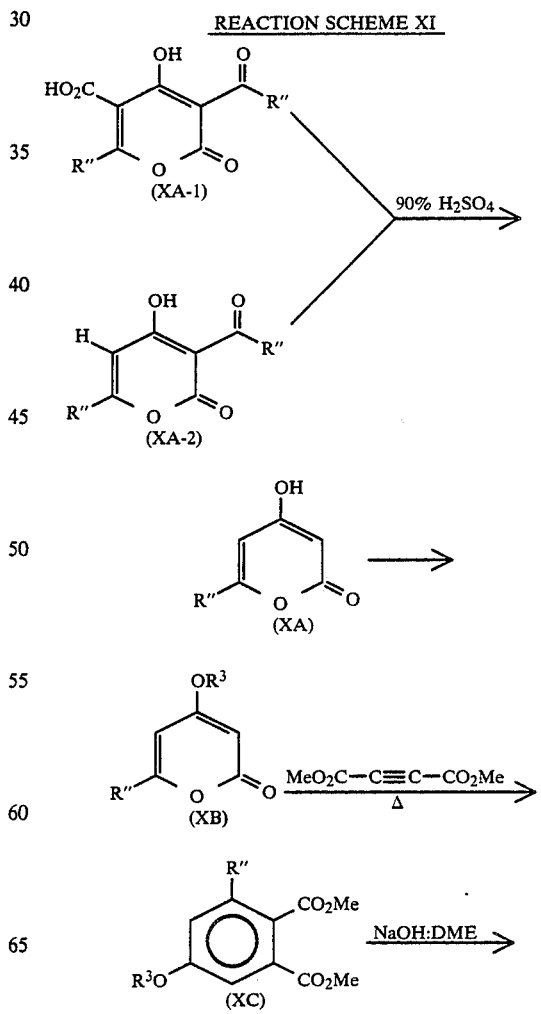

-continued
REACTION SCHEME XI

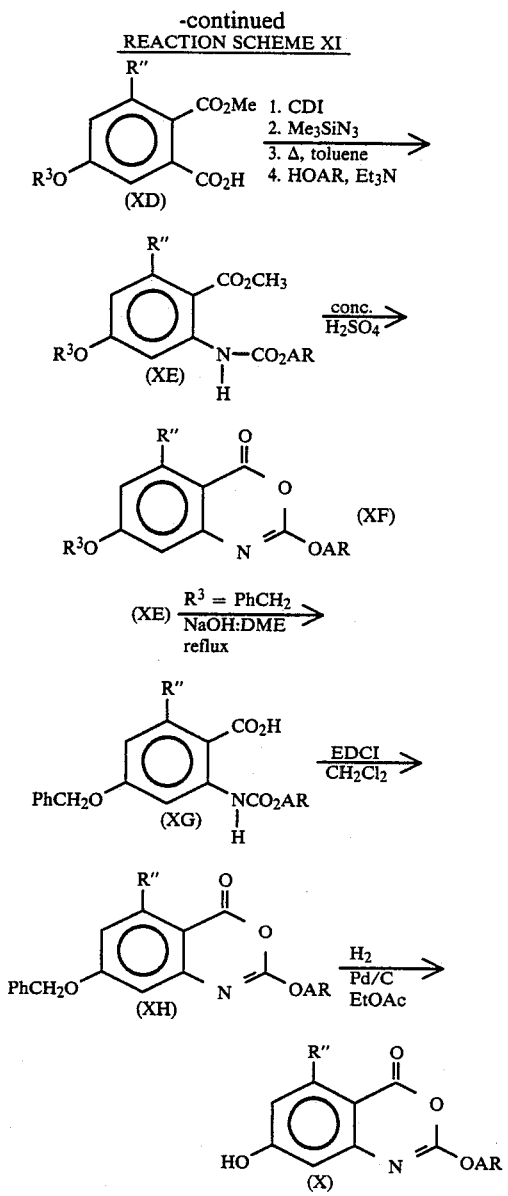

As shown above, a pyrone derivative (XA) is first O-alkylated or O-benzylated to give the pyrone (XB) where $R^3$ is lower alkyl or benzyl. The O-alkylation and O-benzylation of 4-hydroxy-2-pyrone (XA) has been reported by numerous workers. (See J. D. BuLock, H. G. Smith, J. Chem. Soc. 1960, 502–506. E. Suzuki, B. Katsuragawa, S. Inoue, Synthesis 1978, 144–146.) This is carried out employing potassium carbonate as a base and an alkylating agent in 2-butanone at refluxing temperature for 2 to 8 hours, preferably 6 hours. The product is isolated by conventional means. Common alkylation agents are methyl iodide, dimethyl sulphate, ethyl iodide, benzyl bromide, propyl bromide and butyl bromide. Normally, 1 to 3 equivalents of alkylation agents are used. Alternatively, the O-alkylation or O-benzylation reaction can also be carried out in an inert solvent such as HMPA, DMF, THF or a combination of all three, employing sodium hydride or lithium hydride as a base. Common alkylation agent cited above can be used in this experiment. This reaction is normally carried out at room temperature for a period of 1 to 12 hours, normally 10 hours. The product is isolated by conventional means which includes, but not restricted to extraction, column chromatography and recrystallization. Pyrones (XA) and (XB) are commercially available or can be prepared by methods known to those of ordinary skill in the art, e.g., 4-hydroxy-6-methyl-2-pyrone and 4-methoxy-6-methyl-2-pyrone are commercially available from Aldrich Chemical Co. Appropriate pyrones can also be prepared by the following procedures: P. de March, et al., Synthesis 1982, 335–336; M. Moreno-Manas, Synthesis 1984, 430–431; P. de March, et al., J. Heterocyclic. Chem. 1984, 85–89; F. Arndt, Org. Syn. Coll. Vol. III, 231–233, S. S. Deshapande, Indian Chem. Soc. Journal 1948, 9, 303–307; M. Namiki, et al., J. Agr. Chem. Soc. Japan, 25, 472–476, (1951–1952); H. Pechmann, et al., Annalen der Chemie 1948, 273, 186–214. They are prepared by the thermal decomposition of compounds (XA-1) and compounds (XA-2) in 90% sulphuric acid at 110° C.

Diels-Alder reaction between pyrone (XB) and dimethyl acetylene dicarboxylate affords compound (XC). This reaction is normally carried out by heating a mixture of these two reagents at 180° C. to 220° C. for 3 to 4 hours. The preferred conditions are as follows: the reaction is carried out at 180° C. for 2 hours at 210° C. for 1 hour employing 1 to 4 equivalents of dimethyl acetylene dicarboxylate, preferably 1.5 equivalent of dimethyl acetylene dicarboxylate. The resulting product is purified by column chromatography. Compound (XC) is selectively hydrolyzed to give the benzoic acid (XD) with base at room temperature. Normally, 4 to 10% sodium hydroxide and 1,2-dimethoxyethane (1:1 mixture) is used as a solvent. The reaction time ranges from 4 to 16 hours. The organic solvent is removed, the aqueous solution acidified with mineral acids such as dilute hydrochloric acid to give the product. Compound (XD) is isolated by conventional means.

The benzoic acid (XD) is converted to the urethane (XE) by the following reaction sequence: Benzoic acid (XD) is first reacted with 1.1 equivalent of 1,1-carbonyldiimidazole in tetrahydrofuran for 2 hours at room temperature and then at 60° C. for 30 minutes. The reaction mixture is cooled to room temperature. 2–5 equivalents of trimethylsilyl azide (azidotrimethylsilane) is added. The reaction mixture is refluxed for 2 to 3 hours and the tetrahydrofurn removed under reduced pressure. The residue is redissolved in dry toluene and refluxed for 10 to 16 hours, preferably 16 hours. The reaction mixture is cooled and treated with a 5 to 10 equivalents of an alcohol and refluxed for 2 to 4 hours. The product urethane (XE) is isolated by conventional means. Methanol, ethanol, propanol, isopropanol, benzyl alcohol are examples of alcohols that can be used.

Compound (XE) is converted to the 4H-3,1-benzoxazin-4-one (XF) by stirring a solution of compound (XE) in conc. sulphuric acid for a period of 1 to 3 hours, preferably 1 hour. The acid solution is neutralized with an ice-cold suspension of sodium bicarbonate and ethyl acetate. The product (XF) is isolated by conventional means. In cases where $R^3$ is benzyl, the urethane (XE) is first hydrolyzed with base to give the benzoic acid (XG). This hydrolysis reaction is carried out in a 1:1 mixture of 4% sodium hydroxide and 1,2-dimethoxyethane at refluxing temperature of the solvent over a period of 1 to 6 hours, preferably 4 hours. The organic solvent is removed under reduced pressure and the aqueous solution acidified to give acid (XG). Compound (XG) is isolated by conventional means. The acid (XG) is converted to the benzoxazinone (XH) by reacting (XG) with a 1 to 3 fold excess of carbodiimide such as EDCl in an inert solvent such as methylene chloride, tetrahydrofuran or DMF. The product is isolated by conventional means. The benzoxazinone (XH) is hydrogenated to give the 7-hydroxy analog (X). The hydrogenation reaction is carried out employing 10% palladium on charcoal as a catalyst in an inert solvent such as ethyl acetate, 1,2-dimethoxyethane at 50 psi hydrogen on a Parr hydrogenator for a period of 2 to 10 hours, preferably 4 hours. The product is isolated by conventional means.

K. Compounds of Formula A in which a first R' is nitro or amino in the 7-position and a second R' is lower alkyl or lower alkoxy in the 5-position (Formula XI)

The compounds of Formula A which bear an amino R' substituent at the 7-position and a lower alkyl or lower alkoxy R' substituent at the 8-position can be prepared by the procedures set forth in Reaction Scheme XII.

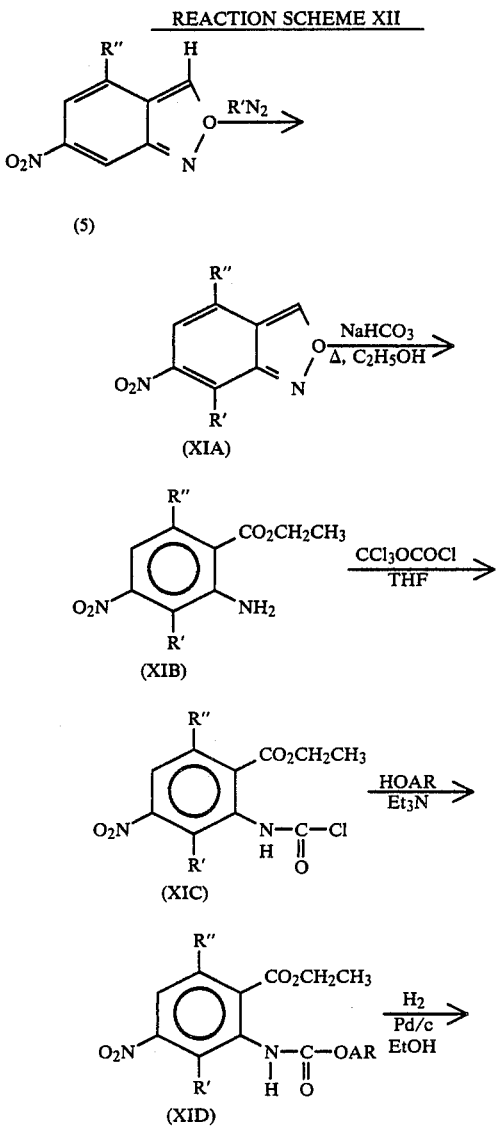

-continued
REACTION SCHEME XII

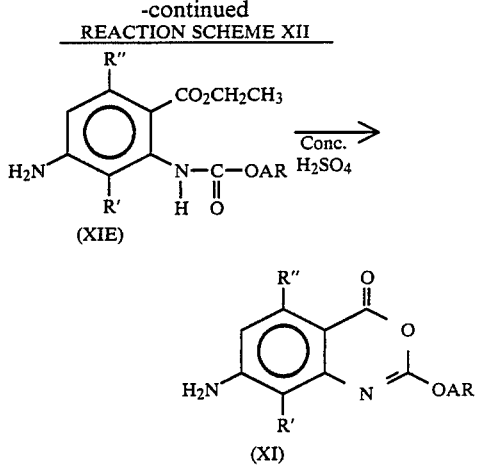

The compound (5) of Reaction Scheme X is converted to the anthranil (XIA) with diazoalkane in ether. This reaction is normally carried out in an inert solvent, such as ether, tetrahydrofuran, preferably anhydrous ether for a period of 8–16 hrs., preferably 12 hours, with 1–4 equivalents of diazoalkane, preferably 4 equivalents at room temperature. The product is isolated by conventional means. Examples of diazoalkane are diazomethane, diazoethane, diazopropane, etc. Diazomethane is prepared according to procedure supplied by Aldrich Chemical Co. (see also T. H. Black, Aldrichimica Acta, Vol. 16, No. 1, pp. 3-10, 1983). Diazoethane, diazopropane and other diazoalkanes can be prepared according to literature procedure. The preparation of diazoalkane in general is reported in *Organic Functional Group Preparations I*, "Chapter 15: Diazo and diazonium compounds," pp 466–496, Eds. S. R. Sandler, W. Karo, Academic Press, 1983. The reaction between diazomethane and 6-nitro-anthranil has also been reported in the literature (see: R. C. Boruah, P. Devi, J. S. Sandhu, *J. Heterocyclic Chem.* 16, pp. 1555-1556, 1979).

Compound (XIA) reacts with base and ethanol to give the 2-amino-benzoate (XIB). This reaction is normally carried out in absolute ethanol as a solvent at refluxing temperature for a period of 2 to 8 hrs., preferably 4 hrs. Potassium carbonate or sodium bicarbonate is normally used as a base. Significantly higher yield of (XIB) is obtained when sodium bicarbonate is used as a base in this reaction. The product is isolated by conventional means. The detail of this reaction is further illustrated in Example 13 below.

The benzoate (XIB) reacts with diphosgene (trichloromethyl chloroformate) and an alcohol in the presence of base to give the urethane (XID). In this reaction, the benzoate (XIB) is first treated with a 0.5 to 0.8 equivalent of trichloromethyl chloroformate (from Alfa Co.) in an inert solvent, preferably tetrahydrofuran or methylene chloride, for 2 to 6 hrs., preferably 2 hrs. to yield the carbamoyl chloride (XIC). Without isolation, this carbamoyl chloride (XIC) is added to a solution of an alcohol and triethylamine in an inert solvent such as tetrahydrofuran or methylene chloride. The product is isolated by conventional means. Normally, a 5–10 equivalent excess of an alcohol is used.

The urethane (XID) is hydrogenated over 10% palladium on charcoal in an inert solvent such as ethanol or ethyl acetate at 30-60 psi. hydrogen over a period of 2–12 hrs., preferably 4 hrs. to give the amino compound (XIE) The product is isolated by conventional means. Compound (XIE) is cyclized in concentrated sulphuric acid over a period of 2–5 hrs., preferably 4 hrs., to give the benzoxazin-4-one (XI). The benzoxazin-4-one is isolated by conventional means after neutralization of the acid with a rapidly stirred mixture of ethyl acetate and saturated sodium bicarbonate solution.

Alternatively, the benzoate (XIB) may be substituted for Formula VII in Reaction Scheme IX to form the corresponding 8-substituted compounds of Formula (IA).

Certain compounds of this invention may be converted to their corresponding pharmaceutically acceptable acid addition salts by virtue of the presence of a basic amine nitrogen. These compounds may be converted from the free base form to various acid addition salts by treating with a stoichiometric excess of the appropriate organic or inorganic acid, such as, for example, phosphoric, pyruvic, hydrochloric or sulfuric acid and the like. Typically, the free base is dissolved in a polar organic solvent such as p-dioxane or dimethoxyethane, and the acid added thereto. The temperature is maintained between about 0° C. and 50° C. The resulting acid addition salt precipitates spontaneously or may be brought out of solution with a less polar solvent.

The acid addition salts of the compounds of Formula I may be decomposed to the corresponding free base by treating with a stoichiometric amount of a suitable base, such as potassium carbonate or sodium hydroxide, typically in the presence of aqueous solvent, and at a temperature of between about 0° C. and 50° C. The free base form is isolated by conventional means, such as extraction with an organic solvent.

Acid addition salts of the compounds of the invention may be interchanged by taking advantage of differential solubilities of the salts, volatilities or acidities of the acids, or by treating with an appropriately loaded ion exchange resin. For example, the interchange is effected by the reaction of a salt of the compounds of Formula I with a slight stoichiometric excess of an acid of a lower pKa than the acid component of the starting salt. This conversion is carried out at a temperature between about 0° C. and the boiling point of the solvent being used as the medium for the procedure.

UTILITY AND ADMINISTRATION

The compounds of Formulas I and A have been shown in standard laboratory tests to inhibit a variety of physiologic enzymes, particularly serine proteases, including human leukocyte elastase, human thrombin, human urokinase, porcine acrosin, porcine pancreatic elastase, bovine cathepsin B, bovine chymotrypsin, and bovine trypsin. Accordingly, the compounds of the invention, their salts, esters, and/or pharmaceutical compositions thereof, may be used in inhibiting, preventing, or controlling physiologic conditions and disease states in animals which are known to involve enzymes, or may be used as contraceptives.

Knowledge of the roles of enzymes in a wide variety of diseases is constantly growing. Recent reviews of the state of the art include "Protein Degradation in Health and Disease", Ciba Foundation Symposium 75, Excerpta Medica, Amsterdam, 1980; "Proteinases in Mammalian Cells and Tissues", A. J. Barrett, ed., North Holland Publishing Company, Amsterdam, 1977; and "Proteases and Biological Control", E. Reich, D. B. Rifkin and E. Shaw, eds., Cold Spring Harbor Laboratory, 1975.

Experimental evidence has revealed the roles of many enzymatic pathways in various physiologic conditions and disease states. Plasminogen activator (PA), a serine protease, causes the conversion of plasminogen to plasmin which in turn is responsible for fibrinolysis. This process is implicated in a number of systems requiring controlled local proteolysis, including inflammation (J. D. Vassalli, et al. *Cell,* 8, 271 [1976]), and cell migration and tissue remodeling, J. E. Valinski, *Cell,* 25, 471 (1981). The production and secretion of PA is also correlated with certain human disorders such as arthritis (Neats, et al., *Nature* [London], 286, 891, 1980; Hamilton, et al., *J. Exp. Med.,* 155, 1702 [1982]) and the expression of transformed phenotypes, D. B. Rifkin, et al., in *Proteases and Biological Control,* D. Rifkin, E. Reich, E. Shaw, eds., Cold Spring Harbor, 1975, pp. 841–847.

There is considerable evidence that plasminogen activator (such as urokinase), leukocyte elastase, and/or related enzymes play a role in tumor cell metastasis (Salo, et al., *Int. J. Cancer,* 30, 669–673, 1973; Kao, et al., *Biochem. Biophys., Res. Comm.,* 105, 383–389, 1982; Powers, J. C., in *Modification of Proteins,* R. E. Feeney and J. R. Whitaker, eds., Adv. Chem. Ser. 198, Amer. Chem. Soc., Wash., D.C., pp 347–367, 1982), suggesting that compounds of this invention may have anti-metastatic activity.

Other evidence suggests an antiparasitic role for the compounds of this invention (Aoki, T., et al., *Mol. Biochem., Parasitol,* 8, 89–97, 1983).

Pulmonary emphysema is a disease characterized by a progressive loss of lung elasticity due to the destruction of lung elastin and alveoli. It is widely held that the destructive changes in lung parenchyma associated with pulmonary emphysema are mediated in large part by unrestrained proteolytic activity in lung connective tissue. (A. Janoff, *Chest,* 83, 54–58 [1983]). A number of proteases have been shown to induce emphysematous lesions in animals when instilled in lungs (V. Marco, et al., *Am. Rev. Respir. Dis.,* 104, 595–8, 1971; P. D. Kaplan, *J. Lab. Clin. Med.,* 82, 349–56 (1973)). In particular, human leukocyte elastase has been shown to produce emphysema in animals (A. Janoff, ibid, 115, 461–78 (1977)). Prophylactic administration of an inhibitor of elastase significantly diminishes the extent of elastase induced emphysema in hamsters (J. Kleinerman, et al., ibid, *Am. Rev. Respir. Dis.,* 121, 381–7, 1980).

Leukocyte elastase and other mediators of inflammation appear to play a role in such acute and high-risk diseases as mucocutaneous lymph node syndrome (Rieger, et al., *Eur. J. Pediatr.,* 140, 92–97, 1983), and adult respiratory distress syndrome (Stockley, R. A., *Clinical Science,* 64, 119–126, 1983; Lee, et al., *N. Eng. J. Med.,* 304, 192–196, 1981; Rinaldo, ibid, 301, 900–909, 1982.

Oral anticoagulants are some of the most important drugs for the prevention and treatment of a variety of venous and, to a lesser extent, arterial thromboembolic disorders (R. A. O'Reilly in the "The Pharmacological Basis of Therapeutics", 6th Ed., A. G. Goodman, L. S. Goodman, A. Gilman, eds., 1980). The enzymes that participate in the cascade leading to blood coagulation are proteases. The coagulation of blood entails the formation of fibrin by the interaction of more than a dozen proteins in a cascading series of proteolytic reactions. Inhibition of these proteinases should block fibrin formation and hence inhibit coagulation. For example, inhibition of thrombin limits the formation of fibrin and is regarded as an approach to thromboembolic therapy.

However, anticoagulants that are in current use and that affect clotting factors do not have a direct onset of action. Consequently, prothrombin time must be monitored, as the degree of Vitamin K antagonism varies from individual to individual.

Thus there is a critical need for new anticoagulants which have a direct onset of action. Pulmonary embolism (PE), for example, is a common complication that usually affects patients who are hospitalized for other medical or surgical problems (A. A. Sasahara, et al., *JAMA*, 249, 2945 (1983) and references therein). The mortality of undiagnosed and therefore untreated PE is relatively high, ranging from about 18% to 35%. Patients undergoing total hip or knee replacement are at extremely high risk for development of deep vein thrombosis, with a reported incidence of 45% to 70% in untreated patients S. Sagar, et al., *Lancet*, 1, 1151 (1978)).

Pancreatitis is a disease which affects large numbers of people including patients having acute alcoholic, acute biliary traumatic and post-operative pancreatitis. Furthermore, with the high incidence of alcoholism, 10,000,000 alcoholics in the U.S. alone, acute and chronic relapsing pancreatitis are seen with increasing frequency. Geokas, et al. has proposed that an effective therapy for acute pancreatitis might be achieved by the use of "a combination of a low molecular weight specific active-site inhibitors for trypsin, chymotrypsin, and elastase", (*Am. J. Pathol.*, 1981, 105, 31–39).

Enzymes possessing cathepsin B-like activity have also received attention because of their extracellular release by neoplastic epithelial cells (Pietras, *J. Histochem. Cytochem.*, 29, 440–450 1981), their presence in the interstitial fluid (Sylven, et al., *Cancer Res.*, 20, 831–836, 1960; Eur. J. Cancer., 463–474, 1968; *Virchows Arch. B. Cell Pathol.*, 17, 97–112, 1974), and in the invasive zone of malignant tissue (R. R. Labrosse, *Mol. Cell Biochem.*, 19, 181–189, 1978) and their enhanced secretion by malignant and metastatic tumors (B. F. Sloane, Cancer Res., 42, 980–986, 1982).

Proteolytic cleavage of precursors is an essential step in the replication of many animal viruses, and there is considerable evidence that protease inhibitors can be effective anti-viral agents (Korant, B. D., (1975) in "Proteases and Biological Control"). Such viruses include influenza (Chirov, O. P. et al. (1981) *Vopr. Virusol.* 6, 677–687). In Sendai virus, for example, a host trypsin-like protease is essential for infectivity (Scheid, A., and Choppin, P. (1975) in "Proteases and Biological Control"). It is reasonable then that compounds of this invention could play a role in amelioration of viral diseases.

Acrosin is a unique serine proteinase which is present in mammalian sperm acrosomes (L. J. D. Zaneveld (1975) in "Proteases and Biological Control", pp. 683–706; R. F. Parrish, *Int. J. Biochem.*, 10, 391–395 (1979)). Since acrosin activity is required for fertilization, it is a rational target for birth control. Further, the inhibition of acrosin is known to prevent fertilization (Zaneveld, L. J. D., et al., (1979), *Biol. Repr.* 20, 1045–1054), supporting a role for acrosin inhibitors as contraceptives.

Initial screening tests to determine enzyme-inhibitory potential can be performed with commercially available enzyme substrates such as peptidyl amides of 4-methyl-7-amino coumarin or 4-nitroaniline. The assays are performed by mixing the substrate and enzyme of interest in an appropriate buffer, and monitoring the rate of enzyme inhibition spectrophotometrically. The reaction rate is monitored continuously either by fluorescence (for coumarin substrates) or absorbance (for nitroanilide substrates) until a constant reaction rate is established. A solution of the compound to be tested in an appropriate solvent, such as a 5 to 20 millimolar solution in dimethyl sulfoxide, is then added, and the increase in fluorescence or absorbance is monitored until a new stable rate is achieved. This is repeated for several concentrations of test compound solution, and the inhibition constant is calculated by non-linear multiple regression fit to the appropriate equation. The compounds of Formula I have been tested in assays of this type and have demonstrated marked inhibitory activity against human leukocyte elastase, human thrombin, human urokinase, porcine acrosin, porcine pancreatic elastase, bovine chymotrypsin and bovine and human trypsin. Some of the compounds of Formula I have also been tested and shown to be active in inhibiting the degradation of basement membrane by macrophages, tumor cells, and elastase. More detailed descriptions of several of these assays may be found in the Examples, below.

Administration of the active compounds and salts described herein can be via any of the accepted modes of administration for systemically active therapeutic medicaments. These methods include oral, parenteral and otherwise systemic, aerosol or topical forms.

Depending on the intended mode of administration, the compositions used may be in the form of solid, semi-solid or liquid dosage forms, such as, for example, tablets, suppositories, pills, capsules, powders, liquids, aerosols, suspensions, or the like, preferably in unit dosage forms suitable for single administration of precise dosages. The compositions will include a conventional pharmaceutical carrier or excipient and an active compound of Formula I or A or the pharmaceutically acceptable salts thereof and, in addition, may include other medicinal agents, pharmaceutical agents, carriers, adjuvants, etc.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Penn., 15th Edition, 1975. The composition or formulation to be administered will, in any event, contain a quantity of the active compound(s) in an amount effective to alleviate the symptoms of the subject being treated.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

For the compounds of Formula I, either oral or nasal (bronchial) administration is preferred, depending on the nature of the disorder being treated.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 1%–95% active ingredient, preferably 25–70%.

Oral and nasal administration to the lungs can also be effected by aerosol delivery forms. For aerosol administration, the active ingredient is preferably supplied in finely divided form along with a surfactant and a propellant. Typical percentages of active ingredients are 0.01 to 20% by weight, preferably 0.04 to 1.0%.

Surfactants must, of course, be non-toxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olestearic and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol (the sorbitan esters sold under the trademark "Spans") and the polyoxyethylene and polyoxypropylene derivatives of these esters. Mixed esters, such as mixed or natural glycerides may be employed. The preferred surface-active agents are the oleates or sorbitan, e.g., those sold under the trademarks "Arlacel C" (Sorbitan sesquioleate), "Span 80" (sorbitan monooleate) and "Span 85" (sorbitan trioleate). The surfactant may constitute 0.1–20% by weight of the composition, preferably 0.25–5%.

The balance of the composition is ordinarily propellant. Liquefied propellants are typically gases at ambient conditions, and are condensed under pressure. Among suitable liquefied propellants are the lower alkanes containing up to five carbons, such as butane and propane; and preferably fluorinated or fluorochlorinated alkanes, such as are sold under the trademark "Freon." Mixtures of the above may also be employed.

In producing the aerosol, a container equipped with a suitable valve is filled with the appropriate propellant, containing the finely divided active ingredient and surfactant. The ingredients are thus maintained at an elevated pressure until released by action of the valve.

For topical administration, these compositions comprise an effective amount of a compound of this class in admixture with a pharmaceutically acceptable non-toxic carrier. A suitable range of composition would be 0.1%–10% active ingredient, and the balance carrier, preferably 1–2% active ingredient. The concentration of active ingredient in pharmaceutical compositions suitable for topical application will vary depending upon the particular activity of the compound used in conjunction with the condition and subject to be treated. Suitable carriers or medicament vehicles for topical application of these compounds include creams, ointments, lotions, emulsions, solutions and the like.

For example, a suitable ointment for topical application of compounds of the invention contains 15 to 45 percent of a saturated fatty alcohol having 16 to 24 carbon atoms such as cetyl alcohol, stearyl alcohol, behenyl alcohol, and the like and 45 to 85 wt. percent of a glycol solvent such as propylene glycol, polyethylene glycol, dipropylene glycol, and mixtures thereof. The ointment can also contain 0 to 15 wt. percent of a plasticizer such as polyethylene glycol, 1,2,6-hexanetriol, sorbitol, glycerol, and the like; 0 to 15 wt. percent of a coupling agent such as a saturated fatty acid having from 16 to 24 carbon atoms, e.g., stearic acid, palmitic acid, behenic acid, a fatty acid amide e.g., oleamide, palmitamide, stearamide, behenamide and an ester of a fatty acid having from 16 to 24 carbon atoms such as sorbitol monostearate, polyethylene glycol monostearate, polypropylene glycol or the corresponding monoester of other fatty acids such as oleic acid and palmitic acid; and 0 to 20 wt. percent of a penetrant such as dimethyl sulfoxide or dimethylacetamide.

The amount of active compound administered will of course, be dependent on the subject being treated, the severity of the affliction, the manner of administration and the judgment of the prescribing physician. However, an effective dosage is in the range of 1–100 mg/kg/day, preferably about 25 mg/kg/day. For an average 70 kg human, this would amount to 70 mg–7 g per day, or preferably about 1.5 g/day.

The following examples serve to illustrate the invention. They should not be construed as narrowing or limiting its scope.

PREPARATION I

Preparation of Substituted anthranilic acids of Formula II

A. Preparation of 4-ethyl anthranilic acid and 6-ethyl-anthranilic acid 4-ethyl anthranilic acid and 6-ethyl anthranilic acid were prepared according to Baker's procedure, as described in *J. Org. Chem.* 17, 141, (1952) and further detailed below.

(i) Preparation of m-ethyl-alpha-isonitrosoacetanilide. In a 5 liter round-bottom flask equipped with overhead stirrer and condensers were placed 74.2 gm. of chloral dihydrate and 900 ml of water. To this solution was then added, sequentially, 107.2 gm of anhydrous sodium sulfate, a solution of 50 gm of m-ethyl aniline dissolved in 248 ml of water and 42 ml of concentrated hydrochloric acid, and lastly, a solution of 90.8 gm of hydroxylamine hydrochloride in 412 ml of water. The mixture was slowly heated over a period of 45 minutes to a temperature of 95° C. The heating mantle was then removed and the flask rapidly cooled to room temperature by immersion in an ice-bath. The crude isonitrosoacetanilide was collected by suction filtration and washed with water. The product was then further purified by the following procedure: The crude isonitrosoacetanilide was dissolved in 500 ml of a 4M sodium hydroxide solution, transferred to a separatory funnel and washed with ether (3×300 ml). The alkaline phase was then treated with charcoal, filtered through Celite and strongly acidified with concentrated hydrochloric acid. The precipitated m-ethyl-alpha-isonitrosoacetanilide was collected by filtration and dried under vacuum, mp. 140°–142° C.

(ii) Preparation of 4-ethyl and 6-ethyl isatin. A 1 liter round-bottom flask containing 370 ml of concentrated sulfuric acid and 30 ml of water was heated to 60° C. m-Ethyl-alpha-isonitrosoacetanilide (64 gm) was added at such a rate as to maintain the temperature between 60° and 65° C. After the addition was completed, the mixture was heated to 80° C. for 10 minutes. The flask was then cooled to room temperature and poured onto 8 to 10 times its volume of ice. After standing for one-half hour, the crude isatin mixture was collected by filtration and washed well with water. The crude extract was then dissolved in about 300 ml of a 3M sodium hydroxide solution by heating on a steam bath, treated with charcoal and filtered through Celite. On acidification to pH 6–7 with concentrated hydrochloric acid, a gummy material appeared and was removed by filtration through Celite. The solution was then acidified to pH 4 and the 4-ethyl isatin was collected by filtration and washed with water: Yield 14.6 gm, mp. 128°–136° C. The cooled filtrate was then strongly acidified with concentrated hydrochloric acid and collected by filtration to give the 6-ethyl isatin: Yield 16.4 gm (28%), mp. 171°–173° C.

(iii) Preparation of 4-ethyl-anthranilic acid.

In a 500 ml flask, was placed 16.84 gm of 6-ethyl isatin which was covered with 216 ml of 1.5M sodium hydroxide solution. With stirring, the mixture was warmed to 50° C. Heating was discontinued and the solution was treated with a 30% solution of hydrogen peroxide (24 ml) which was added at such a rate to maintain the temperature at between 50° to 65° C. The mixture was left to slowly cool to room temperature and was then acidified to pH 4 with concentrated hydrochloric acid. The precipitated product was then collected by filtration: mp. 117°–120° C.; yield 8.93 gm.

(iv) Preparation of 6-ethyl-anthranilic acid. Oxidation of 9.6 gm of 4-ethyl isatin according to the method described in (iii), above, gave 7.3 gm of the title compound: mp. 99°–104° C.

B.

In a similar manner, but replacing m-ethyl aniline with other anilines, the following exemplary compounds of Formula VII are prepared:
6-butyl-anthranilic acid;
4-iodo-anthranilic acid;
6-methyl anthranilic acid;
4,6-dimethyl-anthranilic acid;
3,5-dimethyl-anthranilic acid;
3,5.6-trimethylanthranilic acid;
3,6-dimethylanthranilic acid;
5-butyl-anthranilic acid;
4-methoxy-6-methyl-anthranilic acid; and
4,6-dichloro-anthranilic acid.

C.

Preparation of 6-methoxyanthranilic acid by reduction of the corresponding aromatic nitro compounds was carried out in accordance with Paquette's procedure, J. Am. Chem. Soc., 99, 3734, (1981), mp. 71°–75° C., which can also be used to prepare other 6-alkoxy anthranilic acids.

D.

Preparation of 4-nitro-6-iodo-anthranilic acid and 4-nitro-6-bromo-anthranilic acid are prepared according to the procedure of I. R. Gambir and S. S. Joshi, Indian Chem. Soc. Journal 43–46, (1964). In a similar manner, the following compounds can be prepared:
4-nitro-6-ethyl-anthranilic acid;
4-nitro-6-methyl-anthranilic acid; and
4-nitro-6-propyl-anthranilic acid.

E. Preparation of 5-Alkoxyanthranilic Acid and 5-Alkylthioanthranilic acid

5-Methoxyanthranilic acid and 4-methylthioanthranilic acid were prepared according to the procedure of J. W. Tilley, J. Kudless, R. W. Kierstead, Organic Preparations Procedure Int. 13(3-4), 189–196 (1981).

In a similar manner the following cmpounds are prepared:
5-ethoxy-anthranilic acid;
5-butoxy-anthranilic acid;
5-hexoxy-anthranilic acid;
5-isopropoxy-anthranilic acid:
5-ethylthio-anthranilic acid:
5-methylthio-anthranilic acid;
5-n-pentylthio-anthranilic acid; and
5-n-propylthio-anthranilic acid.

F. Preparation of 4-N,N-Dimethylamino-Anthranilic Acid

4-N,N-dimethylamino-anthranilic acid was prepared according to the procedure of D. H. Klaubert, J. H. Sellstedt, C. J. Guinosso, R. J. Capetola, J. S. C. Bell, J. Med. Chem., 1981, 24, 742–748.

In a similar manner the following compounds are prepared:
4-N,N-diethylamino-anthranilic acid; and
4-N,N-dipropylamino-anthranilic acid.

PREPARATION II

Preparation of Phenyl-, Cycloalkyl- and Alkyl-Chloroformates of Formula III

A. Preparation of N-Butyl Chloroformate

Phosgene was passed into dry ether until saturated (15–20% w/v). n-Butyl alcohol (10 gm) in dry ether (50 ml) was treated with ethereal phosgene (1.1 mol.) at room temperature until the reaction was complete. Removal of the solvent in vacuo gave n-butyl chloroformate in quantitative yield. In representative cases these compounds were purified by distillation, but this is not necessary for the subsequent cyclization. For the preparation of the chloroformates of hindered alcohols, quinoline can be added as a catalyst, quinoline hydrochloride being subsequently removed by filtration.

B.

Thus, in a similar manner, but replacing the n-butyl alcohol with n-hexyl alcohol, s-butyl alcohol, isobutyl alcohol, n-pentyl alcohol, benzyl alcohol, phenol, phenethyl alcohol, 1-phenyl-2-methyl-propanol, 1-phenyl-3-methyl-2-butanol, 1-phenyl-pentanol, salicyl alcohol, procatechol, citronehol, (−)-menthol, cholestanol, and the like, the following compounds of Formula III are prepared:
methyl chloroformate;
ethyl chloroformate;
n-propyl chloroformate;
isopropyl chloroformate;
n-butyl chloroformate;
s-butyl chloroforomate;
isobutyl chlorormate;
n-pentyl chlorformate;
n-hexyl chloroformate;
n-octyl chloroformate;
phenyl chloroformate;
benzyl chloroformate;
phenethyl chloroformate;
1-phenylpentyl chloroformate;
1-phenyloctyl chloroformate;
1-phenyl-2-methyl-propyl chloroformate;
1-phenyl-3-methyl-2-butyl chloroformate;
1-(3-methoxyphenyl)-octyl chloroformate;
1-(4-isobutoxyphenyl)-heptyl chloroformate;
2-carbomethoxyphenyl chloroformate;
(−)-menthyl chloroformate;
cholesteryl chloroformate;
cyclopropyl chloroformate;
cyclobutyl chloroformate;
cyclohexyl chloroformate;
1-cyclopropyl-ethyl chloroformate;
1-cyclobutyl-methyl chloroformate;
1-cyclohexyl-propyl chloroformate;
1-(2-ethylcyclohexyl) methyl chloroformate;
1-(4-nitrocyclohexyl)-pentyl chloroformate; and
1-(2-dimethylaminobenzyl) chloroformate.

PREPARATION III

Preparation of Acid Anhydrides of Formula IV

A. Preparation of butyric anhydride

Molar quantities of butyric acid and butyryl chloride are heated together on a water-bath for 1 hour and then boiled for 7 hours in an oil-bath. Butyric anhydride, b.p. 198°–199° C./765 mm, is obtained on distillation of the resulting mixture.

B.

In a similar manner, but starting instead with acetyl chloride and sodium acetate, acetic anhydride is obtained.

C.

In like manner, other symmetrical and mixed acid anhydrides are obtained from the corresponding free acids and acid chlorides, or alternatively from the acid chlorides and alkali salts of the carboxylic acids, including;
hexanoic anhydride; and
acetic propionic anhydride.

PREPARATION IV

Preparation of Ethyl 2-amino-6-ethyl-4-nitrobenzoate and Related Compounds of Formula VII A. Preparation of 2,4-dinitro-6-ethylphenol (i) Concentrated sulfuric acid (25g) was added to 2-ethylphenol (25 g, Aldrich) with swirling. The solution was heated on a steam bath for one hour, cooled and 25 ml water added. The solution was placed in a dropping funnel and added dropwise to 70% nitric acid (40 g), with cooling provided by an ice-salt bath cooled by glycol. The solution in the dropping funnel was added over 1.5 to 2 hours, with the temperature kept below 0° C. The resulting mixture was stirred at 0° C. for three hours, the ice bath removed, and the mixture further stirred overnight at room temperature. The mixture was then heated on a steam bath for one hour, cooled and 50 ml of water added. Following extracted with diethyl ether, the ether layer was washed with brine, dried over $MgSO_4$ and evaporated to a dark oil which was columned on silica gel using 10% ethyl acetate-petroleum ether. The combined filtrates gave a yellow-orange oil, which solidified upon being pumped dry to give 2,4-dinitro-6-ethylphenol, yield 34 gm.

(ii) Proceeding in a similar matter but starting instead with 2-propylphenol, 2,4-dinitro-6-propylphenol was obtained as an oil.

(iii) Similarly prepared are the following compounds of Formula 2:
2,4-dinitro-6-isopropylphenol;
2,4-dinitro-6-butylphenol; and
2,4-dinitro-6-isobutylphenol.

B. Preparation of 1-chloro-2,4-dinitro-6-ethylbenzene (i) 2,4-Dinitro-6-ethylphenol (10 g) was placed in a 250 ml round bottom flask, and phosphorous oxychloride (60 ml, Fisher) was added. N,N-diethylamiline (15 ml, Aldrich) was added portionwise, and the mixture became hot. The flask was placed under a condenser equiped with a drying tube heated on a steam bath for two hours and cooled. The mixture was then carefully poured onto ice, with stirring and extracted with ethyl acetate. The ethyl acetate layer was washed with brine, dried over $MgSO_4$ and evaporated to a dark oil which was columned on silica gel using 10% ethyl acetate petroleum ether. The evaporated filtrates gave a reddish oil, which solidified upon being pumped dry. The solid was recrystallized from ethyl acetate-petroleum ether to give pale yellow needles of 1-chloro-2,4-dinitro-6-ethylbenzene.

Yield: 8.1 g, m.p. 41°–44° C.

IR: 3400 $cm^{-1}$, 3090 $cm^{-1}$, 2980 $cm^{-1}$, 1800 $cm^{-1}$, (w), 1540 $cm^{-1}$, 1345 $cm^{-1}$.

(ii) Proceeding in a similar manner, the following compounds of Formula 3 were prepared:
1-chloro-2,4-dinitro-6-methylbenzene; and
1-chloro-2,4-dinitro-6-propylbenzene.

(iii) Similarly, but starting instead with other appropriate corresponding compounds of Formula 2, the following compounds of Formula 3 are prepared:
1-chloro-2,4-dinitro-6-isopropylbenzene;
1-chloro-2,4-dinitro-6-butylbenzene; and
1-chloro-2,4-dinitro-6-isobutylbenzene.

C. Preparation of (6-ethyl-2,4-dinitrophenyl)-diacetylmethane (i) Sodium methoxide (8.16 g) was placed in a flask contain hexamethylphosphoramide (50 ml, Aldrich). 2,4-pentanedione (50 ml, Aldrich) was added and the mixture stirred while gently heated with a heating mantle (Variac 25/140) for thirty minutes. 6-Ethyl-2,4-dinitrochlorobenzene (10 g) in some dry tetrahydrofuran was added, and the mixture heated at the same setting for two more hours. The reaction mixture was cooled and partitioned between ethyl acetate and 5N hydroclhoric acid.

The ethyl acetate layer was washed with 5N HCl, water and brine, dried over MgSO$_4$ and evaporated to a dark oil. 350 ml of 10% ethyl acetate-petroleum ether was added, and a pale ywellow solid precipitated out. This was columned on silica gel using 20% ethyl acetate-petroleum ether to give 5.4 g of (2,4-dinitro-6-ethyl)-diacetylmethane, m.p.: 126°–128° C., IR: 3100 cm$^{-1}$, 2980 cm$^{-1}$, 1525 cm$^{-1}$, 1345 cm$^{-1}$.

(ii) Proceeding in the same manner, the following compounds of Formula 4 were prepared:
(6-methyl-2,4-dinitrophenyl)-diacetylmethane, m.p. 145°–147° C.; and
(6-propyl-2,4-dinitrophenyl)-diacetylmethane, m.p. 147°–147.5° C.

(iii) In like manner, but substituting other corresponding compounds of Formula 3, the following compounds of Formula 4 are prepared:
(6-isopropyl-2,4-dinitrophenyl)-diacetylmethane;
(6-butyl-2,4-dinitrophenyl)-diacetylmethane; and
(6-isobutyl-2,4-dinitrophenyl)-diacetylmethane.

D. Preparation of 4-ethyl-6-nitro-anthranil (i) (6-ethyl-2,4-dinitrophenyl)-diacetylmethane (5 g) was dissolved in concentrated sulfuric acid and heated to 90°–110° C. in an oil bath for three hours. The mixture was poured onto ice, with stirring, and extracted with methylene chloride. The resulting emulsion was filtered through Celite to separate the layers. The methylene chloride layer was dried over MgSO$_4$ and evaporated to a dark solid which was re-dissolved in some methylene chloride and columned on silica using 10% ethyl acetate-petroleum ether. Evaporation of the filtrate 2.57 g of 4-ethyl-6-nitro-anthranil as an orange solid, m.p. 69°–72° C., IR: 3140 cm$^{-1}$, 3100 cm$^{-1}$, 2970 cm$^{-1}$, 1550 cm$^{-1}$, 740 cm$^{-1}$.

(ii) Proceeding in the same manner, but starting with other appropriate compounds of Formula 4, the following compounds of Formula 5 were prepared:
4-methyl-6-nitro-anthranil, m.p. 158°–160° C.; and
4-propyl-6-nitro-anthranil, m.p. 82°–84° C.

(iii) In like manner, the following compounds of Formula 5 are prepared:
4-isopropyl-6-nitro anthranil;
4-butyl-6-nitro anthranil; and
4-isobutyl-6-nitro anthranil.

E. Preparation of Ethyl-2-amino-6-ethyl-4-nitrobenzoate (i) 4-ethyl-6-nitro anthranil (2 g) was refluxed for three hours in ethanol with potassium carbonate. The reaction mixture was cooled, filtered and evaporated to a dark oily solid which was dissolved in ethyl acetate and dried. The residue was re-dissolved in methylene chloride and columned on silica gel using 15% ethyl acetate-petroleum ether. The residue from the filtrate was recrystallized from methylene chloride-petroleum ether to give 1.9 g ethyl-2-amino-6-ethyl-4-nitrobenzoate, m.p. 68°–70° C., IR: 3490 cm$^{-1}$, 3380 cm$^{-1}$, 3080 cm$^{-1}$, 2980 cm$^{-1}$, 1690 cm$^{-1}$, 1620 cm$^{-1}$, 1515 cm$^{-1}$, 1350 cm$^{-1}$.

(ii) Proceeding in the same manner, but starting instead with other appropriate, 4-alkyl-6-nitro anthranils of Formula 5, the following compounds of Formula VII were prepared:
ethyl 2-amino-6-methyl-4-nitrobenzoate, m.p. 67°–68° C.; and
ethyl 2-amino-6-propyl-4-nitrobenzoate, m.p. 78°–79° C.

(iii) In like manner, the following compounds of Formula VII are prepared:
ethyl-2-amino-6-isopropyl-4-nitrobenzoate;
ethyl-2-amino-6-butyl-4-nitrobenzoate; and
ethyl-2-amino-6-isobutyl-4-nitrobenzoate.

PREPARATION V

Preparation of Ethyl 2-carbethoxyamino-6-ethyl-4-nitro-benzoate and Related Compounds of Formula VIII

A. Preparation of Ethyl 2-carbethoxyamino-6-ethyl-4-nitro-benzoate

A solution of ethyl-2-amino-6-ethyl-4-nitro-benzoate (400 mg) in ethyl acetate (10 ml) was added dropwise to a solution of trichloromethyl chloroformate in ethylacetate (10 ml). A precipitate was formed immediately which dissolved on prolonged sitrring for 2½ hours. A solution of ethanol (5 ml) and triethylamine (5 ml) was added. A yellowish precipitate was formed. After 1 hour the solution was partitioned between ethylacetate and water. The ethylacetate layer was washed with brine solution, dried over magnesium sulfate and evaporated to a reddish oil. The material was further purified by column chromatography on silica gel (10% EtOAc:-pet.ether) to give a solid material, m.p. 47°–48° C., IR: 1530, 1710, 1740, 1610 cm$^{-1}$.

B.

Proceeding in a similar manner but replacing the 2-amino-6-ethyl-4-nitro-benzoate with other appropriate corresponding compounds of formula VII, prepared as described in Preparation IV and replacing the ethanol with other appropriate alcohols, as desired, the following compounds of Formula VIII are prepared:
ethyl 2-carbobenzyloxyamino-6-ethyl-4-nitro-benzoate;
ethyl 2-carboethoxyamino-6-methyl-4-nitro-benzoate;
ethyl 2-carboisopropoxyamino-6-propyl-4-nitro-benzoate; and
ethyl 2-carbocyclopropyloxyamino-6-isobutyl-4-nitro-benzoate.

PREPARATION VI

Preparation of 2-carboethoxyamino-4-nitro-6-ethyl benzoic acid and Related Compounds of Formula IX

A. Preparation of 2-carboethoxyamino-4-nitro-6-ethyl benzoic acid

A solution of ethyl 2-carboethoxyamino-4-nitro-6-ethyl-benzoate in tetrahydrofuran (10 ml) and sodium hydroxide (20 ml, 10%) was stirred at room temperature for 20 hours. The solution was extracted with ethyl acetate. The aqueous layer was acidified to pH=1 with 6M HCl, and then immediately extracted with ethylacetate. The ethyl acetate extract was washed with water and dried over magnesium sulphate. Solvent evaporation gave a solid which was further recrystallized from methylene chloride:petroleum ether to yield 2-carboethoxyamino-4-nitro-6-ethyl benzoic acid, m.p. 121°–123° C. as orange crystals: IR: 1665, 1720, 1620, 1510, 2500–3200(br), 3500 cm$^{-1}$.

B.

Proceeding in a similar manner, but replacing the 2-carboethoxyamino-4-nitro-6-ethyl-benzoate with other compounds of Formula VIII, the preparation of which is described in Preparation V above, the following compounds of Formula VIX are prepared:
2-carbobenzyloxyamino-6-ethyl-4-nitro-benzoic acid;
2-carboethoxyamino-6-methyl-4-nitro-benzoic acid;
2-carboisopropoxy-amino-6-propyl-4-nitro-benzoic acid;
2-carboisopropoxyamino-6-butyl-4-nitrobenzoic acid; and
2-carbocyclopropyloxyamino-6-isobutyl-4-nitrobenzoate.

PREPARATION VII

Preparation of Substituted Pyrones of Formula XA

A. Preparation of 3-Propionyl-4-hydroxy-5-carboxy-6-ethyl-2-pyrone

3-Propionyl-4-hydroxy-5-carboxy-6-ethyl-2-pyrone was prepared according to the procedure of M. Mamiki (see M. Namiki, K. Nakamura, (I. Hayashida, Y. Niikawa, K. Yamamoto, C. Nakamura, R. Shimose, J. Agr. Chem. Soc. Japan 25, 472-6, 1951-1952.) The following procedure is representative:

Acetone dicarboxylic acid (9 gm) was added portionwise to propionyl anhydride (36 gm) and cooled in an ice-bath. The reaction temperature was kept at 0° C., while concentrated sulphuric acid (1 ml) was added dropwise. After 30 minutes at room temperature, the reaction mixture was heated in a water bath at 60° C. A clear solution was formed. The reaction mixture was poured onto ice. A yellow precipitate was formed and was filtered. The crude material was recrystallized from methanol to give 3-Propionyl-4-hydroxy-5-carboxy-6-ethyl-2-pyrone (8 gm).

B. Preparation of 3-propionyl-4-hydroxy-6-ethyl-2-pyrone 3-propionyl-4-hyroxy-6-ethyl-2-pyrone was prepared from a base-catalyzed dimerization of methyl propionylacetate according to the procedure of F. Arndt, Org. Syn. Coll. Vol. III, 231-233). This procedure is further detailed below.

Methyl propionylacetate (25 ml) and sodium bicarbonate (1 gm) were place in a distillation apparatus. The mixture was heated by a heating mantle. The internal temperature of the reaction mixture rose slowly from 165° C. to 210° C. over a period of 6.5 hours. Methanol (6.5 ml) was collected as a distillate. The dark brown reaction mixture was vacuum distilled with an air condenser. The product was distilled at 105°-107° C. (1 mm Hg) and solidified to yield 3-propionyl-4-hydroxy-6-ethyl-2-pyrone (3.7 gm).

C. Preparation of 3-(3-methylpropionyl)-4-hydroxy-6-isobutyl-2-pyrone 3-(3-methylpropionyl)-4-hydroxy-6-isobutyl-2-pyrone was prepared according to the procedure as cited under Section A of this Preparation. An illustrative procedure was as follows:

Concentrated sulphuric acid (0.5 ml) was added dropwise to isovaleryl chloride (10 gm) at 0° C. Acetone-1,3-dicarboxylic acid was added portionwise. The ice-bath was removed. The solution was stirred at room temperature for 30 minutes. HCl gas was evolved and a white foamy material was formed. The flask was then heated on a steam bath for 30 minutes. More HCl gas was evolved. A reddish-brown solution was formed. This solution was cooled and left to crystallize. An orange crystal was formed and was filtered. The solid residue was washed with ice-cold water. A solution of this solid was treated with charcoal and recrystallized to yield 3-(3-methylpropionyl)-4-hydroxy-6-isobutyl-2-pyrone. IR (KBr): 2980, 1750, 1725, 1535 cm$^{-1}$.

D. Preparation of 4-Hydroxy-6-ethyl-2-pyrone

A solution of 3-propionyl-4-hydroxy-5-carboxy-6-ethyl-2-pyrone (7 gm) in concentrated sulphuric acid (14 ml) and water (2 ml) was heated in an oil bath set at 120° C. for 2 hours. The solution was cooled and then poured into ice. The insoluble solid was filtered. The filtrate was extracted with ethyl acetate (3×100 ml). The combined organic layer was dried over magnesium sulphate and evaporated to give a dirty brown solid. The combined solid from the filtration and the extraction was purified by flash column chromatography (Whatman LPS-II silica gel, elution gradient: 40 to 80% ethyl acetate:pet. ether 30-60) to give 4-hydroxy-6-ethyl-2-pyrone, which was further purified by recrystallization from ether. (Yield: 2.7 gm), m.p. 106°-108° C.

E.

Proceeding in a similar manner, the following compounds are prepared:
4-hydroxy-6-propyl-2-pyrone,
4-hydroxy-6-isobutyl-2-pyrone, and
4-hydroxy-6-butyl-2-pyrone.

F.

Proceeding in a similar manner as described in Section D of this example, 3-(3-methylpropionyl)-4-hydroxy-5-isobutyl-2-pyrone was converted to 4-hydroxy-6-isobutyl-2-pyrone. M.p. 110°-111° C., IR (KBr): 3300-2700, 1705, 1680-1660, 1585 cm$^{-1}$.

PREPARATION VIII

Preparation of 4-Methoxy-6-ethyl-2-pyrone and Related Compounds of Formula XB

A. Preparation of 4-Methoxy-6-ethyl-2-pyrone

A suspension of 4-hydroxy-4-ethyl-2-pyrone (360 mg, 0.00257 mol), dimethyl sulphate (0.3 ml) and potassium carbonate (1 gm) in 2-butanone was heated at reflux with stirring for 7 hours. The mixture was cooled, filtered and the filtrate was evaporated to give an oil. This oil was further purified by column chromatography (Whatman LPS-II silica gel, 30% ethyl acetate:pet. ether 30-60) to yield 4-methoxy-6-ethyl-2-pyrone (370 mg), m.p. 54°-55° C., IR (KBr): 1730, 1710, 1650, 1570 cm$^{-1}$. Anal. calcd. for $C_8H_{10}O_3$: C, 62.33, H, 6.54. Found: C, 62.26, H, 6.55.

B. Preparation of 4-Benzyloxy-6-methyl-2-pyrone

Sodium hydride (2.2 gm, 50% oil, 0.0458 mol) was added portionwise to a solution of 4-hydroxy-6-methyl-2-pyrone (5 gm, 0.0396 mol) in anhydrous tetrahydrofuran. When the gas evolution ceased, anhydrous DMF (80 ml) was added, along with tetra-n-butylammonium iodide (1 gm). The solution was stirred at room temperature for 30 minutes. A solution of benzyl bromide (5.2 ml, 0.0425 mol) in HMPA (5 ml) was added. After 16 hours at room temperature, the volatile component was removed by evaporation. DMF was removed under high vacuum (1 mm Hg). The residual oil was partitioned between 10% HCl and ethyl acetate. The ethyl acetate layer was dried over magnesium sulphate and evaporated to an oil. This material was purified by flash column chromatography (Whatman LPS-II silica gel, elution gradient: 10–50% ethyl acetate:pet. ether 30–60; product R$_f$=0.4 at 30% ethyl acetate:pet. ether 30–60). The material was recrystallized from ether to give 4-benzyloxy-6-methyl-2-pyrone (3.42 gm, 40% yield), m.p. 90°–91° C.; IR (KBr): 1740, 1575, 1650 cm$^{-1}$, Anal. calcd. for C$_{13}$H$_{12}$O$_3$: C, 72.21, H, 5.59. Found: C, 72.31, H, 5.64.

C.

Proceeding in the same manner, the following compounds were made:
4-benzyloxy-6-ethyl-2-pyrone: m.p. 62°–63° C., IR (KBr): 1730, 1640–1660, 1565 cm$^{-1}$. Anal. calcd. for C$_{14}$H$_{14}$O$_3$: C, 73.03, H, 6.13. Found: C, 72.99, H, 6.13;
4-buty-6-ethyl-2-pyrone; oil, IR (neat): 1710–1730, 1645, 1560 cm$^{-1}$. Mass spect.: 196 (M+), 167 (M+-Et), 141, 111;
4-propoxy-6-ethyl-2-pyrone: yellow oil; and
4-benzyloxy-6-isobutyl-2-pyrone: m.p. 64°–65° C., IR (KBr): 1730, 1700, 1645, 1565 cm$^{-1}$.

D.

Proceeding in a similar manner, the following compounds are made from the corresponding pyrones:
4-benzyloxy-6-propyl-2-pyrone;
4-benzyloxy-6-butyl-2-pyrone;
4-benzyloxy-6-phenyl-2-pyrone;
4-benzyloxy-3,6-dimethyl-2-pyrone;
4-benzyloxy-3,6-dimethyl-2-pyrone; and
4-benzyloxy-6-isopropyl-2-pyrone.

PREPARATION IX

Preparation of 4-Benzyloxy-6-methyl-phthalate and Related Compounds of Formula XC A. Preparation of 4-Benzyloxy-6-methyl-phthalate A mixture of dimethyl acetylene dicarboxylate (3.4 gm, 0.0239 mol) and 4-benzyloxy-6-methyl-2-pyrone (5.5 gm, 0.0254 mol) was heated in an oil bath at 180° C. for 1 hour and then at 210° C. for 2 hours. The reaction mixture was cooled and the brown residue dissolved in methylene chloride. The crude material was purified by column chromatography (silica gel 60, 30% ethyl acetate: pet. ether 30–60) to give the impure title compound. This material was further purified by column chromatography (Whatman LPS-11 silica gel, elution gradient: 10% to 30% ethyl acetate: pet. ether 30–60) to give 4-benzyloxy-6-methyl-phthalate (R$_f$=0.25, 15% ethyl acetate: pet. ether 30–60, yield: 2.9 gm) as oil. IR (neat): 1725, 1600 cm$^{-1}$. Mass spect.: 314 (M+), 283 (M+-OMe), 255 (M+-COOMe), 192 (M+-OMe-C$_7$H$_7$), 91 (C$_7$H$_7$).

B.

Proceeding in the same manner, the following compounds were made:
Dimethyl 4-benzyloxy-6-ethyl-phthalate: m.p. 66°–67° C., IR (KBr): 1720–1730, 1600 cm$^{-1}$;
Dimethyl 4-methoxy-6-methyl-phthalate: oil, IR (neat): 1720, 1600 cm$^{-1}$. Mass spect.: 238 (M+), 207 (M+-OMe), 179 (M+-COOMe), 164, 148;
Dimethyl 4-methoxy-6-methyl-phthalate: oil, IR (neat): 1720, 1600 cm$^{-1}$. Mass spect.: 238 (M+), 207 (M+-OMe), 179 (M+-COOMe), 164, 148;
Dimethyl 4-methoxy-6-ethyl-phthalate: colorless oil, IR (neat): 1725–1740, 1605, 1430 cm$^{-1}$;
Dimethyl 4-propoxy-6-ethyl-phthalate: oil; and
Dimethyl 4-butoxy-6-ethyl-phthalate: oil, IR (neat): 1725, 1600 cm$^{-1}$. Mass spect.: 294 (M+), 262 (M+-MeOH), 263, 264, 247, 204, 148.

C.

Proceeding in the same manner, the following compounds were made:
Dimethyl 4-benzyloxy-6-propyl-phthalate;
Dimethyl 4-benzyloxy-6-butyl-phthalate;
Dimethyl 4-benzyloxy-6-isobutyl-phthalate;
Dimethyl 4-benzyloxy-6-phenyl-phthalate; and
Dimethyl 4-benzyloxy-3,6-dimethyl-phthalate.

PREPARATION X

Preparation of 2-Carbomethoxy-3-methyl-5-benzyloxy-benzoic Acid and Related Compounds of Formula XD A. Preparation of 2-carbomethoxy-3-methyl-5-benzyloxy-benzoic acid A solution of dimethyl 4-benzyloxy-6-methyl-phthalate (1.5 gm) in sodium hydroxide (2% solution, 12 ml) and 1,2-dimethoxyethane (12 ml) was stirred at room temperature for 4 hours. The solvent was removed under reduced pressure. The aqueous solution was washed with ethyl acetate (3×125 ml). The organic extract was dried over magnesium sulphate and evaporated to give a solid. This solid was recrystallized from ethyl acetate: pet. ether 30–60 to yield 2-carbomethoxy-3-methyl-5-benzyloxy-benzoic acid (750 mg), m.p. 132°–133° C., IR (KBr): 2500–3200, 1725, 1685, 1600 cm$^{-1}$. Anal. calcd. for C$_{17}$H$_{16}$O$_5$: C, 67.99, H, 5.37. Found: C, 68.01, H, 5.42.

B.

Proceeding in a similar manner, the following compounds were made:
2-carbomethoxy-3-ethyl-5-benzyloxy-benzoic acid: m.p. 135°–136° C., IR (KBr): 3500–3300, 2700–3200 (br.) 1735, 1690, 1600, 1500 cm$^{-1}$;
2-carbomethoxy-3-ethyl-5-methoxy-benzoic acid: m.p. 116°–118° C., IR (KBr): 2500–3300, 1730, 1690, 1600 cm$^{-1}$; anal. calcd. for C$_{12}$H$_{14}$O$_5$: C, 60.50, H, 5.92; found C, 60.57, H, 5.97;
2-carbomethoxy-3-ethyl-5-propoxy-benzoic acid: m.p. 99°–100° C., IR (KBr): 3350–3650, 2975, 1740, 1725, 1690, 1605 cm$^{-1}$; anal. calcd. for C$_{12}$H$_{14}$O$_5$: C, 60.50, H, 5.92; found C, 60.57, H, 5.97;
2-carbomethoxy-3-ethyl-5-methoxy-benzoic acid: m.p. 146°–147° C., IR (KBr): 2500–3200 (br.), 1740, 1690, 1605 cm$^{-1}$; anal. calcd. for C$_{11}$H$_{12}$O$_5$: C, 58.93, H, 5.39; found C, 58.94, H, 5.41; and
2-carbomethoxy-3-methyl-5-butoxy-benzoic acid: m.p. 81°–82° C., IR (KBr): 2500–3100, 1740, 1690, 1600 cm$^{-1}$.

C.

Proceeding in a similar manner, the following compounds are made:
2-carbomethoxy-3-propyl-5-benzyloxy-benzoic acid;
2-carbomethoxy-3-phenyl-5-benzyloxy-benzoic acid;
2-carbomethoxy-3-isobutyl-5-benzyloxy-benzoic acid;
2-carbomethoxy-3-butyl-5-benzyloxy-benzoic acid;
2-carbomethoxy-3,6-dimethyl-5-benzyloxy-benzoic acid; and
2-carbomethoxy-3-isobutyl-5-methoxy-benzoic acid.

PREPARATION XI

Preparation of 2-(isopropoxy)carbonylamino-4-benzyloxy-6-methyl-benzoate and Related Compounds of Formula XE

A. Preparation of 2-(isopropoxy)carbonylamino-4-benzyloxy-6-methyl-benzoate To a solution of 2-carbomethoxy-3-methyl-5-benzyloxy-benzoic acid (392 mg, 0.0013 mol) in tetrahydrofuran under argon, 1,1-carbonyl-diimidazole (268 mg, 0.0016 mol) was added. The resulting solution was stirred at room temperature for 2 hours and refluxed for 30 minutes. The solution was cooled to room temperature, azidotrimethylsilane (0.2 ml) was added; the resulting solution was refluxed for 2 hours. Tetrahydrofuran was removed under reduced pressure. Dry toluene (35 ml) was added, the solution was refluxed for 16 hours and cooled. Isopropyl alcohol (1 ml) was added, and the resulting solution was refluxed for 4 hours. The solution was evaporated to dryness. The residual oil was partitioned between ethyl acetate and water. The organic layer was dried over magnesium sulphate and evaporated to give a solid. This solid was further purified by column chromatography (10% $CH_2Cl_2$: pet. ether 30–60 to 70% $CH_2Cl_2$: pet. ether) to give 2-(isopropoxy)carbonylamino-4-benzyloxy-6-methyl-benzoate (220 mg).

B.

Proceeding in a similar manner, the following compound was made:
Methyl 2-ethoxycarbonylamino-4-methoxy-6-methyl benzoate, m.p. 85°–86° C.; anal. calcd. for $C_{13}H_{17}NO_5$: C, 58.42, H, 6.44; found: C, 58.55, H, 6.43.

C.

Proceeding in a similar manner, the following compounds are made:
Methyl 2-ethoxycarbonylamino-4-methoxy-6-ethyl benzoate;
Methyl 2-ethoxycarbonylamino-4-ethoxy-6-ethyl benzoate;
Methyl 2-ethoxycarbonylamino-4-benzyloxy-6-ethyl benzoate;
Methyl 2-ethoxycarbonylamino-4-benzyloxy-6-methyl benzoate; and
Methyl 2-ethoxycarbonylamino-4-methoxy-6-isobutyl benzoate;

PREPARATION XII

Preparation of 2-(Isopropoxy)carbonylamino-4-benzyloxy-6-methyl-benzoic acid and Related Compounds of Formula XG

A. Preparation of 2-(Isopropoxy)carbonylamino-4-benzyloxy-6-methyl-benzoic acid A solution of methyl 2-isopropoxycarbonylamino-4-benzyloxy-6-methyl-benzoate (171 mg, 0.000487 mol) in sodium hydroxide (4% solution, 10 ml) and 1,2-dimethoxyethane (10 ml) was refluxed for 4 hours and then left at room temperature overnight. The organic solvent was removed under reduced pressure, the aqueous extract was acidified to pH 3 with 5% hydrochloric acid. A white suspension was formed which was extracted with ethyl acetate. The ethyl acetate layer was dried over magnesium sulphate and evaporated to give a solid. This solid was further purified by column chromatography (50% ethyl acetate: pet. ether) to give 2-(isopropoxy)carbonylamino-4-benzyloxy-6-methyl-benzoic acid (97 mg), m.p. 137°–139° C., IR (CHCl₃): 2500–3200, 1721, 1660, 1610, 1585, 1520 cm⁻¹; H-NMR (acetone-d₆): 1.9 (d, 6H, C$\underline{H}_3$CHC$\underline{H}_3$), 3.10 (s, 3H, Me), 5.4 (m, 1H, CH₃C$\underline{H}$CH₃), 5.4 (s, 2H, PhCH₂), 7.2 (m, 1H, ArH), 8.0 (m, 5H, Ph).

B.

Proceeding in a similar manner, the following compounds are made:
2-(isopropoxy)carbonylamino-4-benzyloxy-6-ethyl-benzoic acid;
2-(isopropoxy)carbonylamino-4-benzyloxy-6-propyl-benzoic acid;
2-(isopropoxy)carbonylamino-4-benzyloxy-6-isobutyl-benzoic acid;
2-ethoxycarbonylamino-4-benzyloxy-6-methyl-benzoic acid; and
2-ethoxycarbonylamino-4-benzyloxy-6-ethyl-benzoic acid.

PREPARATION XIII

Preparation of 4-ethyl-7-methyl-6-nitro-anthranil and Related Compounds of Formula XIA

A. Preparation of 4-ethyl-7-methyl-6-nitro-anthranil

A solution of 4-ethyl-6-nitro-anthranil, (1.5 gm, 0.0577 mol.) in anhydrous ether (50 ml) was mixed with an ethereal solution of diazomethane (100 ml, conc. 1 gm CH₂N₂/80 ml) and stirred for 16 hrs. The excess diazomethane was removed by pouring the reaction mixture over a short column of silica gel and eluting the column with ether. The ethereal solution was evaporated to give a yellow solid and this solid was purified by column chromatography (40% methylene chloride: pet. ether 30–60) to yield 4-ethyl-7-methyl-6-nitro-anthranil as a solid. The solid was recrystallized from 10% ether: pet ether 30–60, Yield: 1.145 gm. mp. 68°–69° C., IR (CHCl₃): 2980, 1625, 1550, 1460 cm⁻¹. H-NMR (CDCl₃): 1.40 (t, 3H, CH₃), 2.80 (s, 3H, CH₃), 2.90 (q, 1H, CH₂), 7.30 (br. s, 1H, H5), 9.30 (s, 1H, H3).

B.

Proceeding in a similar manner, the following compound was made:
4,7-dimethyl-6-nitro-anthranil, yellow oil, IR (neat); 3120, 1725, 1625, 1550, 1510 cm⁻¹.

C.

Proceeding in a similar manner, the following compounds are made:
4-methyl-7-ethyl-6-nitro-anthranil;
4-ethyl-7-ethyl-6-nitro-anthranil;
4-propyl-7-ethyl-6-nitro-anthranil;
4-isopropyl-7-methyl-6-nitro-anthranil; and
4-isopropyl-7-ethyl-6-nitro-anthranil.

PREPARATION XIV

Preparation of Ethyl 2-Amino-6-ethyl-3-methyl-4-nitro-benzoate and Related Compounds of Formula XIB

A. Preparation of Ethyl 2-Amino-6-ethyl-3-methyl-4-nitro-benzoate

A solution of 4-ethyl-7-methyl-6-nitro-anthranil (300 mg, 0.000146 mol.) in absolute ethanol was mixed with sodium bicarbonate (160 mg, 0.0019 mol.) and was refluxed for 4 hrs. The solution was evaporated to dryness, the residue partitioned between ethyl acetate and 5% hydrochloric acid solution. The organic layer was dried over magnesium sulphate and evaporated to give a solid. This solid was further purified by column chromatography (10% ethyl acetate: pet. ether 30–60) to give ethyl 2-amino-6-ethyl-3-methyl-4-nitro-benzoate as an oil (yield: 276 mg, 76%). IR (neat): 3500, 3400, 2980, 1700, 1620, 1580, 1530 cm$^{-1}$. H-NMR (CDCl$_3$): 1.20 (t, 3H, CH$_3$), 1.40 (t, 3H, CH$_3$), 2.18 (s, 3H, CH$_3$) 2.78 (q, 3H, CH$_2$), 4.40 (q, 2H, CH$_2$O), 5.05 (br.s, 2H, NH$_2$), 6.91 (s, 1H, ArH).

B.

Proceeding in a similar manner, the following compound was made:
Ethyl 2-amino-6-ethyl-3-methyl-4-nitro-benzoate, IR (neat): 3550, 3400, 2980, 1690, 1610, 1590, 1520$^{-1}$ cm.

C.

Proceeding in a similar manner, the following compounds are made:
Ethyl 2-amino-6-propyl-3-methyl-4-nitro-benzoate;
Ethyl 2-amino-6-isopropyl-3-methyl-4-nitro-benzoate;
Ethyl 2-amino-6-methyl-3-ethyl-4-nitro-benzoate;
Ethyl 2-amino-3,6-diethyl-4-nitro-benzoate; and
Ethyl 2-amino-6-isopropyl-3-ethyl-4-nitro-benzoate;

PREPARATION XV

Preparation of Ethyl 6-ethyl-3-methyl-2-ethoxycarbonylamino-4-nitrobenzoate and Related Compounds of Formula XID

A. Preparation of ethyl 6-ethyl-3-methyl-2-ethoxycarbonylamino-4-nitrobenzoate A solution of ethyl 2-amino-3-methyl-6-ethyl-4-nitro-benzoate (70 mg, 0.000277 mol) in anhydrous tetrahydrofuran (5 ml) was added slowly to a solution of trichloromethyl chloroformate (43 mg) in tetrahydrofuran (5 ml). The solution was stirred for 2 hrs. at room temperature and then added slowly to a solution of ethanol (1 ml), triethylamine (0.05 ml) in tetrahydrofuran (5 ml). The resulting mixture was sitirred for 2 hrs. and evaporated to dryness. The residue was partitioned between ethyl acetate and water. The organic layer was dried over magnesium sulphate and evaporated to dryness. This material was purified by thick layer plate chromatography to yield ethyl 6-ethyl-3-methyl-2-ethoxycarbonylamino-4-nitrobenzoate. Yield: 35 mg, IR (CHCl$_3$): 3420, 1730, 1530, 1500 cm$^{-1}$. H-NMR: 1.10–1.50 (overlapping peaks [3t], 9H, CH$_3$CH$_2$, CH$_3$CH$_2$O, CH$_3$CH$_2$O), 2.31 (s, 3H, CH$_3$), 2.70 (q, 2H, CH$_3$CH$_2$Ar), 4.20 (q, 2H, CH$_2$O), 4.40, (q, 2H, CH$_2$O), 6.60 (br.s, 1H, NH), 7.69 (s, 1H, ArH).

B.

Proceeding in a similar manner, the following compounds are made:
Ethyl 2-ethoxycarbonylamino-3,6-dimethyl-4-nitro-benzoate;
Ethyl 2-ethoxycarbonylamino-3-methyl-6-propyl-4-nitro-benzoate;
Ethyl 2-methoxycarbonylamino-3-methyl-6-propyl-4-nitro-benzoate;
Ethyl 2-ethoxycarbonylamino-3-methyl-6-propyl-4-nitro-benzoate;
Ethyl 2-isopropoxycarbonylamino-3-methyl-6-ethyl-4-nitro-enzoate;
Ethyl 2-isopropoxycarbonylamino-3-methyl-6-isopropyl-4-nitro-benzoate;
Ethyl 2-ethoxycarbonylamino-3-methyl-6-isopropyl-4-nitro-benzoate;
Ethyl 2-ethoxycarbonylamino-3,6-diethyl-4-nitro-benzoate; and
Ethyl 2-ethoxycarbonylamino-3-ethyl-6-propyl-4-nitro-benzoate.

PREPARATION XVI

Preparation of Ethyl 4-amino-2-ethoxycarbonylamino-6-ethyl-3-methyl-benzoate and Related Compounds of Formula XIE

A. Preparation of ethyl 4-amino-2-ethoxycarbonylamino-6-ethyl-3-methyl-benzoate A solution of ethyl 2-ethoxycarbonylamino-6-ethyl-3-methyl-4-nitro-benzoate (35 mg) in absolute ethanol (80 ml) was hydrogenated over 10% palladium on charcoal at 50 psi. hydrogen on a Parr hydrogenator for 5 hrs. The catalyst was removed by suction filtration through Celite. The filtrate was evaporated to give an oil which was further purified by thick layer chromatography (30% ethyl acetate: pet. ether 30–60) to give ethyl 4-amino-2-ethoxycarbonylamino-6-ethyl-3-methyl-benzoate as a white solid (30 mg). IR (CH$_2$Cl$_2$): 3340, 1700 (br.), 1600 cm$^{-1}$. H-NMR (CD$_3$OD): 1.00–1.50 (overlapping peaks [3t], 9H, CH$_3$CH$_2$, 2CH$_3$CH$_2$O), 2.00 (s, 3H, CH$_3$), 2.60 (q, 2H, CH$_2$Ar), 4.15 (q, 2H, CH$_2$), 4.30 (q, 2H, CH$_2$), 6.60 (s, 1H, ArH).

B.

Proceeding in a similar manner, the following compounds are prepared:
Ethyl 4-amino-2-ethoxycarbonylamino-3,6-dimethyl-benzoate;
Ethyl 4-amino-2-ethoxycarbonylamino-3,6-diethyl-benzoate;
Ethyl 4-amino-2-isopropoxycarbonylanino-3,6-dimethyl-benzoate;
Ethyl 4-amino-2-methoxycarbonylamino-3-methyl-6-ethyl-benzoate;
Ethyl 4-amino-2-ethoxycarbonylamino-3-methyl-6-isopropyl-benzoate; and
Ethyl 4-amino-2-isopropoxycarbonylamino-3-methyl-6-isopropyl-benzoate.

EXAMPLE I

A. Synthesis of 2-ethoxy-4H-3,1-benzoxazin-4-one, and Related Compounds of Formula IA To a solution of anthranilic acid (0.1 mol., 13.71 gm) in dry pyridine (100 ml) at room temperature under anhydrous conditions was added ethyl chloroformate (4 equiv., 38.25 ml) in a dropwise manner over 15 minutes. After stirring for 2 hours, excess pyridine was removed under reduced pressure at 40° C. (bath temperature) and the residue was stirred vigorously in ice cold water (250 ml) for 15 minutes. The pale yellow powder was collected by filtration, washed with water (100 ml), and air-dried to give 18.6 gm of crude product. The crude product was treated with active charcoal (2 gm) in ethyl acetate (150 ml) to afford a white solid after removal of solvent. Recrystallization from EtOAc-ether gave 17.02 (89%) of the title compound, 2-ethoxy-4H-3,1-benzoxazin-4-one, as colorless crystals; m.p. 88°–90.5° C.; IR (KBr): $\nu_{max}$ 1760 cm$^{-1}$ (C=O), 1630 cm$^{-1}$ (C=N); H"NMR (CDCl$_3$); δ 1.46 ppm (t, J=7.1 Hz, 3H,)CH$_2$C$\underline{H}_3$), 4.53 ppm (q, J=7.1 Hz, 2H, OC$\underline{H}_2$CH$_3$), 7.30–8.20 ppm (m, 4H, aromatic protons).

B.

In a similar manner, but substituting other appropriately substituted anthranilic acids (which may be commercially obtained or prepared as described in Preparation I, above), for the anthranilic acid, the following substituted compounds of Formula IA were prepared:

2-ethoxy-5-methyl-4H-3,1-benzoxazin-4-one, m.p. 104°–105° C.;
2-ethoxy-5-ethyl-4H-3,1-benzoxazin-4-one, m.p. 89°–91° C.;
2-ethoxy-6-methylthio-4H-3,1-benzoxzazin-4-one, m.p. 67°–68.5° C.;
6-dimethylamino-2-ethoxy-4H-3,1-benzoxazin-4-one, m.p. 93°–95° C.;
7-carboethoxyamino-2-ethoxy-4H-3,1-benzoxazin-4-one, m.p. 191°–193° C.;
6,7-dimethoxy-2-ethoxy-4H-3,1-benzoxazin-4-one, m.p. 169°–170° C.;
2-ethoxy-7-nitro-4H-3,1-benzoxazin-4-one, m.p. 106°–109° C.;
7-dimethylamino-2-ethoxy-4H-3,1-benzoxazin-4-one, m.p. 196°–198° C.;
2-benzyloxy-4H-3,1-benzoxazin-4-one; m.p. 88°–89.5° C.; and
2-benzyloxy-6,7-dimethoxy-4H-3,1-benzoxazin-4-one, m.p. 152°–154° C.

C.

In like manner, but replacing the ethyl chloroformate in Paragraph A, above, with other corresponding chloroformates of Formula III, (which may be commercially obtained, or prepared as described in Preparation II, above), the following compounds of Formula IA are prepared:

2-methoxy-4H-3,1-benzoxazin-4-one;
2-n-propoxy-4H-3,1-benzoxazin-4-one;
2-isopropoxy-4H-3,1-benzoxazin-4-one;
2-n-butoxy-4H-3,1-benzoxazin-4-one;
2-s-butoxy-4H-3,1-benzoxazin-4-one;
2-isobutoxy-4H-3,1-benzoxazin-4-one;
2-n-pentoxy-4H-3,1-benzoxazin-4-one;
2-n-hexoxy-4H-3,1-benzoxazin-4-one;
2-n-octyloxy-4H-3,1-benzoxazin-4-one;
2-phenyloxy-4H-3,1-benzoxazin-4-one;
2-benzyloxy-4H-3,1-benzoxazin-4-one;
2-phenethyloxy-4H-3,1-benzoxazin-4-one;
2-phenylbutyloxy-4H-3,1-benzoxazin-4-one;
2-phenyloctyloxy-4H-3,1-benzoxazin-4-one;
2-(1-phenyl-2-methyl-propyl)oxy-4H-3,1-benzoxazin-4-one;
2-(1-phenyl-3-methyl-2-butyl)oxy-4H-3,1-benzoxazin-4-one;
2-(1-(3-methoxyphenyl)octyloxy-4H-3,1-benzoxazin-4-one;
2-(1-(4-isobutoxyphenyl)heptyloxy-4H-3,1-benzoxazin-4-one;
2-(4-ethylbenzyl)oxy-4H-3,1-benzoxazin-4-one;
2-(3,5-dimethoxybenzyl)oxy-4H-3,1-benzoxazin-4-one;
2-carbomethoxyphenyloxy-4H-3,1-benzoxazin-4-one;
2-citronyloxy-4H-3,1-benzoxazin-4-one;
2-(−)-methoxy-4H-3,1-benzoxazin-4-one;
2-cholesteryloxy-4H-3,1-benzoxazin-4-one;
2-cyclopropyloxy-4H-3,1-benzoxazin-4-one;
2-cyclobutyloxy-4H-3,1-benzoxazin-4-one;
2-cyclohexylyoxy-4H-3,1-benzoxazin-4-one;
2-cyclopropylbutyloxy-4H-3,1-benzoxazin-4-one;
2-(4-methylthiocyclohexyl)butyloxy-4H-3,1-benzoxazin-4-one;
2-(3-methylpentoxy)-4H-3,1-benzoxazin-4-one;
2-5-methylhexyloxy)-4H-3,1-benzoxazin-4-one;
2-(3-methyl-4-ethylpentyl)oxy-4H-3,1-benzoxazin-4-one;
2-(2-methylpentyl)oxy-4H-3,1-benzoxazin-4-one;
2-(1-[2-ethylcyclohexyl]methyl)oxy-4H-3,1-benzoxazin-4-one;
2-(1-[4-nitrocyclohexyl]pentyl)oxy-4H-3,1-benzoxazin-4-one;
2-(1-[2-methylthiocyclopentyl]ethyl)oxy-4H-3,1-benzoxazin-4-one; and
2-(2-dimethylaminobenzyl)oxy-4H-3,1-benzoxazin-4-one.

D.

Similarly, but further replacing the unsubstituted anthranilic acid with appropriate substituted anthranilic acids of Formula II, (which may be commercially obtained, or can be prepared as described in Preparation I, above), the following compounds of Formula IA are prepared:

2-methoxy-5-methyl-4H-3,1-benzoxazin-4-one;
2-isopropoxy-5-ethyl-4H-3,1-benzoxazin-4-one;
2-n-butoxy-5-methyl-7-methoxy-4H-3,1-benzoxazin-4-one;
2-s-butoxy-5-methylthio-4H-3,1-benzoxazin-4-one;
2-isobutoxy-5-chloro-4H-3,1-benzoxazin-4-one;
2-n-hexoxy-7-ethoxy-4H-3,1-benzoxazin-4-one;
2-n-octyloxy-5-methyl-7-nitro-4H-3,1-benzoxazin-4-one;
2-phenyloxy-5-ethyl-4H-3,1-benzoxazin-4-one;
2-benzyloxy-5-methyl-4H-3,1-benzoxazin-4-one;
2-phenethyloxy-5,7-dimethoxy-4H-3,1-benzoxazin-4-one;
2-phenylbutyloxy-6-methylthio-4H-3,1-benzoxazin-4-one;
2-phenyloctyloxy-5-methyl-6,7-dichloro-4H-3,1-benzoxazin-4-one;
2-(1-phenyl-2-methyl-propyl)oxy-5-isopropoxy-4H-3,1-benzoxazin-4-one;
2-(1-phenyl-3-methyl-2-butyl)oxy-5-methyl-4H-3,1-benzoxazin-4-one;
2-(1-(4-isobutoxyphenyl)heptyloxy-5-methyl-7-methoxy-4H-3,1-benzoxazin-4-one;
2-(4-ethylbenzyl)oxy-4H-3,1-benzoxazin-4-one;
2-(3,5-dimethoxybenzyl)oxy-4H-3,1-benzoxazin-4-one;
2-cyclopropyloxy-5-ethyl-4H-3,1-benzoxazin-4-one;
2-cyclobutyloxy-6-methylthio-4H-3,1-benzoxazin-4-one;
2-cyclohexyloxy-5-isopropyl-4H-3,1-benzoxazin-4-one;

2-(5-methylhexyloxy)-4H-3,1-benzoxazin-4-one;
2-(3-methyl-4-ethylpentyl)oxy-4H-3,1-benzoxazin-4-one;
2-(2-methylpentyl)oxy-7-nitro-4H-3,1-benzoxazin-4-one;
2-(1-[4-aminocyclohexyl]methyl)oxy-6-iodo-4H-3,1-benzoxazin-4-one; and
2-(1-N,N-dimethylaminobenzyl)oxy-6-N,N-dimethylamino-4H-3,1-benzoxazin-4-one.

E.

Similarly, the following nitro-substituted 2-oxy-4H-3,1-benzoxazin-4-ones of Formula IA are prepared from the correspondingly substituted nitro-substituted anthranilic acids. (4-nitro-anthranilic acid is commercially available. Alternatively, these, as well as the 5- and 6-nitro anthranilic acids can be prepared according to the method set forth in Preparation I, above.):
2-ethoxy-7-nitro-4H-3,1-benzoxazin-4-one;
2-benzyloxy-7-nitro-4H-3,1-benzoxazin-4-one;
2-phenethyloxy-5-ethyl-7-nitro-4H-3,1-benzoxazin-4-one;
2-cyclopropyloxy-5-propyl-7-nitro-4H-3,1-benzoxazin-4-one;
2-cyclobutyloxy-5-thiomethyl-7-nitro-4H-3,1-benzoxazin-4-one;
2-cyclohexyloxy-6-nitro-4H-3,1-benzoxazin-4-one;
2-phenylbutyloxy-7-nitro-4H-3,1-benzoxazin-4-one;
2-cyclopropylbutyloxy-5-methyl-7-nitro-4H-3,1-benzoxazin-4-one;
2-(4-ethylbenzyl)oxy-5-methyl-7-nitro-4H-3,1-benzoxazin-4-one;
2-(3,5-dimethoxybenzyl)oxy-5-iodo-7-nitro-4H-3,1-benzoxazin-4-one;
2-(4-thiomethylcyclohexyl)butyloxy-7-nitro-4H-3,1-benzoxazin-4-one;
2-methoxy-5-nitro-4H-3,1-benzoxazin-4-one;
6-nitro-2-propoxy-4H-3,1-benzoxazin-4-one;
5-methyl-7-nitro-2-pentoxy-4H-3,1-benzoxazin-4-one;
2-hexoxy-6-nitro-4H-3,1-benzoxazin-4-one;
8-nitro-2-(3-methylpentoxy)-4H-3,1-benzoxazin-4-one; and
2-isobutoxy-5-bromo-7-nitro-4H-3,1-benzoxazin-4-one.

EXAMPLE II

A. Synthesis of
7-Amino-2-ethoxy-4H-3,1-benzoxazin-4-one, and Related Compounds of Formula IB 7-Nitro-2-ethoxy-4H-3,1-benzoxazin-4-one (1 gm, 4.2 m mol.), 10% Pd-C (1 gm), and cyclohexane (2.5 ml) were refluxed in dry benzene (50 ml) under anhydrous conditions for 3 hours. The hot reaction mixture was filtered immediately through celite and the catalyst on celite was washed with hot benzene (25 ml). The combined filtrate was evaporated to dryness under reduced pressure. The residue was stirred in anhydrous ether (30 ml) to give 410 mg (47%) of the title compound, 7-amino-2-ethoxy-4H-3,1-benzoxazin-4-one, as a pale yellow powder, after filtration. The product can be further purified by chromatography on silica gel column, if necessary (silica gel 60; EtOAc:pet. ether=1:2); m. p. 185°-187° C.; IR (KBr): $\nu_{max}$ 3425, 3330 cm$^{-1}$ (NH$_2$), 1740 cm$^{-1}$ (C=O), 1640 cm$^{-1}$ (C=N); H'NMR (CDCl$_3$): δ1.43 ppm (t, J=7.1 Hz, 3H, OCH$_2$CH$_3$), 4.30 ppm (b, 2H, NH$_2$), 4.75 ppm (q, J=7.1 Hz, 2H, OC$\underline{H}_2$CH$_3$), 6.5–7.98 ppm (m, 3H, aromatic protons).

B.

In a similar manner, but replacing the 3-ethoxy-7-nitro-benzoxazin-4-one with other corresponding nitro-substituted compounds of Formula IA, (which are prepared as described in Example I, paragraphs D and E, above), the following compounds of Formula IB are prepared:
7-amino-2-ethoxy-4H-3,1-benzoxazin-4-one;
7-amino-2-benzyloxy-4H-3,1-benzoxazin-4-one;
8-amino-2-ethoxy-4H-3,1-benzoxazin-4-one;
6-amino-2-benzyloxy-4H-3,1-benzoxazin-4-one;
2-cyclopropyloxy-6,8-diamino-4H-3,1-benzoxazin-4-one;
5-amino-2-cyclobutyloxy-7-thiomethyl-4H-3,1-benzoxazin-4-one;
6-amino-2-cyclohexyloxy-4H-3,1-benzoxazin-4-one;
7-amino-2-phenylbutyloxy-4H-3,1-benzoxazin-4-one;
7-amino-2-(4-thiomethylcyclohexyl)butyloxy-4H-3,1-benzoxazin-4-one;
5-amino-2-methoxy-4H-3,1-benzoxazin-4-one;
6-amino-2-propoxy-4H-3,1-benzoxazin-4-one;
6,7-diamino-2-butoxy-4H-3,1-benzoxazin-4-one;
7-amino-5-methyl-2-pentoxy-4H-3,1-benzoxazin-4-one;
7-amino-2-hexoxy-4H-3,1-benzoxazin-4-one;
8-amino-2-(3-methylpentoxy)-4H-3,1-benzoxazin-4-one; and
7-amino-2-isobutoxy-6-chloro-4H-3,1-benzoxazin-4-one;
7-ethyl-7-amino-2-ethoxy-4H-3,1-benzoxazin-4-one; and
5-propyl-7-amino-2-benzyloxy-4H-3,1-benzoxazin-4-one.

C.

In a similar manner, but replacing the 2-ethoxy-7-nitro-4H-3,1-benzoxazin-4-one with 2-ethoxy-5-ethyl-7-nitro-4H-3,1-benzoxazin-4-one the following compound of Formula IB was prepared: 2-ethoxy-5-ethyl-7-amino-4H-3,-benzoxazin-4-one, IR: 3440, 3360, 3240, 1735, 1660, 1640, 1610 cm$^{-1}$.

D.

Similarly, but starting with other corresponding 5-alkyl-7-nitro-substituted compounds of Formula IA, (which are prepared as described in Example XII, Paragraphs A, B and C), the following compounds of Formula IB are prepared:
2-ethoxy-5-methyl-7-amino-4H-3,1-benzoxazin-4-one;
2-ethoxy-5-propyl-7-amino-4H-3,1-benzoxazin-4-one;
2-ethoxy-5-isopropyl-7-amino-4H-3,1-benzoxazin-4-one;
2-ethoxy-5-butyl-7-amino-4H-3,1-benzoxazin-4-one; and
2-ethoxy-5-isobutyl-7-amino-4H-benzoxazin-4-one.

EXAMPLE III

A. 7-acetylamino-2-ethoxy-4H-3,1-benzoxazin-4-one, and Related Compounds of Formula IC 7-Amino-2-ethoxy-4H-3,1-benzoxazin-4-one (0.48 m mol., 100 mg) was stirred in acetic anhydride (5 ml) at room temperature under anhydrous conditions for 30 minutes. The excess acetic anhydride was removed under reduced pressure at 35° C. (bath temperature). The residue was dissolved in EtOAc (20 ml) and washed with saturated sodium bicarbonate solution (15 ml), water (15 ml). The organic layer was dried (MgSO$_4$) and evaporated to give the crude product. Chromatography on silica gel 60 (EtOAc:pet. ether=3:2) gave 85 mg (71%) of the title compound, 7-acetylamino-2-ethoxy-4H-3,1-benzoxazin-4-one as a white powder; m. p. 245°-246° C.; IR (KBr): $\nu_{max}$3360 cm$^{-1}$ (NH), 1740 cm$^{-1}$ (C=O), 1620 cm$^{-1}$ (C=N), 1590 cm$^{-1}$ (aromatic amide); H'NMR (CDCl$_3$): δ1.44 ppm (t, J=711 Hz, 3H, OCH$_2$CH$_3$), 2.24 ppm (s, 3H, CH$_3$CO), 4.51 ppm (q, J=7.1 Hz, 2H, OCH$_2$CH$_3$), 7.30 ppm (b, 1H, NH), 7.28–8.10 ppm (m, 3H, aromatic protons).

B.

In a similar manner, but substituting other appropriate acid anhydrides (which are commercially available, or can be prepared as set forth in Preparation III, above) for the acetic anhydride, and other corresponding nitro-substituted compounds of Formula IB (prepared as described in Example I, paragraph E) the following compounds of Formula IC are prepared:
5-acetylamino-2-ethoxy-4H-3,1-benzoxazin-4-one;
5-acryloylamino-2-ethoxy-4H-3,1-benzoxazin-4-one;
6-acetylamino-2-benzyloxy-4H-3,1-benzoxazin-4-one;
2-benzyloxy-6-butyrylamino-4H-3,1-benzoxazin-4-one;
5-crotonoylamino-2-cyclobutyloxy-7-thiomethyl-4H-3,1-benzoxazin-4-one;
6-acetylamino-2-cyclohexylyoxy-4H-3,1-benzoxazin-4-one;
2-cyclohexylyoxy-6-hexanoylamino-4H-3,1-benzoxazin-4-one;
7-acetylamino-2-phenylbutyloxy-4H-3,1-benzoxazin-4-one;
8-acetylamino-2-cyclopropylbutyloxy-5-methyl-4H-3,1-benzoxazin-4-one;
8-acryloylamino-2-cyclopropylbutyloxy-5-methyl-4H-3,1-benzoxazin-4-one;
7-acetylamino-2-(4-thiomethylcyclohexyl)butyloxy-4H-3,1-benzoxazin-4-one;
5-acetylamino-2-methoxy-4H-3,1-benzoxazin-4-one;
6-acetylamino-2-propoxy-4H-3,1-benzoxazin-4-one;
6-butyrylamino-2-propoxy-4H-3,1-benzoxazin-4-one;
7-acetylamino-5-methyl-2-pentoxy-4H-3,1-benzoxazin-4-one;
6-acetylamino-2-hexoxy-4H-3,1-benzoxazin-4-one; and
8-acetylamino-2-(3-methylpentoxy)-4H-3,1-benzoxazin-4-one.

EXAMPLE IV

A.
6-Carboethoxyamino-2-ethoxy-4H-3,1-benzoxazin-4-one and Related Compounds of Formula ID To a solution of 7-amino-2-ethoxy-4H-3,1-benzoxazin-4-one (0.2 m mol., 41 mg) and dry pyridine (0.1 ml) in dry dichloromethane (4 ml) at room temperature under anhydrous conditions was added ethyl chloroformate (0.05 ml, 0.52 m mol.) in one portion. After stirring for one hour, the reaction mixture was diluted with dichloromethane (16 ml), washed successively with water (15 ml), 5% CuSO$_4$) and evaporated to dryness. The residue was stirred in anhydrous ether (2 ml) and filtered to afford 53 mg (95%) of the title compound, 7-carboethoxyamino-2-ethoxy-4H-3,1-benzoxazin-4-one as a colorless powder; m.p. 191°-193° C.; IR (KBr): $\nu_{max}$ 3310 cm$^{-1}$(NH), 1735 cm$^{-1}$ (ester, carbamyl); 1640 cm$^{-1}$ (C=N); H'NMR (CDCl$_3$): δ1.34 ppm (t, J=7.1 Hz, 3H, CH$_3$CH$_2$OCON), 1.44 ppm (t, J=7.1 Hz, 3H, CH).

B.

In a similar manner, but replacing the 2-ethoxy-7-nitro-4H-3,1-benzoxazin-4-one with other 7-nitro-substituted compounds of Formula IA (which can be prepared according to the method of Example I, paragraph E,) and substituting other suitable acid halides of Formula III for the chloroformate, the following compounds of Formula ID are prepared:
5-carbomethoxyamino-2-ethoxy-4H-3,1-benzoxazin-4-one;
5-carboethoxyamino-2-ethoxy-4H-3,1-benzoxazin-4-one;
2-benzyloxy-6-carboethoxyamino-4H-3,1-benzoxazin-4-one;
2-benzyloxy-6-carbopropoxyamino-4H-3,1-benzoxazin-4-one;
6-carbobutoxyamino-2-cyclohexyloxy-4H-3,1-benzoxazin-4-one;
6-carboethoxyamino-2-cyclohexylyoxy-4H-3,1-benzoxazin-4-one;
7-carbomethoxyamino-2-phenylbutyloxy-4H-3,1-benzoxazin-4-one;
8-carboethoxyamino-2-cyclopropylbutyloxy-5-methyl-4H-3,1-benzoxazin-4-one;
8-carbopropoxyamino-2-cyclopropylbutyloxy-5-methyl-4H-3,1-benzoxazin-4-one;
7-carboethoxyamino-2-(4-thiomethylcyclohexyl)-butyloxy-4H-3,1-benzoxazin-4-one;
5-carbomethoxyamino-2-methoxy-4H-3,1-benzoxazin-4-one;
6-carboethoxyamino-2-propoxy-4H-3,1-benzoxazin-4-one; and
6-carbomethoxyamino-2-propoxy-4H-3,1-benzoxazin-4-one.

EXAMPLE V

A.
7-(3-Diethylureido)-2-ethoxy-4H-3,1-benzoxazin-4-one and Related Compounds of Formula IE Trichloromethyl chloroformate (0.1 m mol., 13.3 μl) was added to a solution of 7-amino-2-ethoxy-4H-3,1-benzoxazin-4-one (21 mg, 0.1 m mol) in dry THF (3 ml) at room temperature under argon. After stirring for 30 minutes dry pyridine (0.1 ml) and diethylamine (0.1 ml) were added to the reaction mixture and the stirring was continued for an additional 15 minutes. The mixture was diluted with dichloromethane (20 ml) and washed successively with water (15 ml), 5% CuSO$_4$ solution (2×10 ml), water (15 ml). The organic layer was dried (MgSO$_4$) and evaporated to give a semi-solid residue. The residue was stirred in anhydrous ether (2 ml) and filtered to afford 12 mg (39%) of the expected carbamate derivative; m.p. 163°-164.5° C. IR (KBr): $\nu_{max}$ 3380 cm$^{-1}$ (NH), 1740 and 1730 cm$^-$(C=O), 1670 CM$^{-1}$ (urea), 1640 cm$^{-1}$ (C—N); H'NMR (CDCl$_3$): 1.26 ppm (t, J=7.2 Hz, 6H, (CH$_3$CH$_2$)$_2$N), 1.43 ppm (t, J=7.2 Hz, 3H, CH$_3$CH$_2$O), 3.41 ppm (q, J=7.2 Hz, 4H, (CH$_3$CH$_2$)$_2$N), 4.50 ppm (q, J=7.2 Hz, 2H, CH$_3$CH$_2$O), 6.59 ppm (b, 1H, NH), 7.29–8.06 ppm (m, 3H, aromatic protons).

B.

In a similar manner, but starting with the same or other amino-substituted compounds of Formulas IA and IB, and replacing the ethylamine where appropriate with other alkylamines, the following compounds of Formula IE are prepared:

7-(3-dimethylureido)-2-ethoxy-4H-3,1-benzoxazin-4-one; and 7-(3-methylureido)-5-methyl-2-ethoxy-4H-3,1-benzoxazin-4-one.

EXAMPLE VI

A. Preparation of 5-Bromomethyl-2-ethoxy-4H,3,1-benzoxazin-4-one and Related Compounds of Formula IF$_1$ A solution of 2-ethoxy-5-methyl-4H-3,1-benzoxazin-4-one (330 mg), N-bromosuccinimide (340 mg) and AIBN (10 mg, 2,2′-azobis-iso-butyronitrile) was refluxed for 2½ hours. The solution was evaporated to dryness. The residue was purified by column chromatography (silica gel) 10% ethyl acetate:petroleum ether 30–60). This afforded the title compound, 5-bromomethyl-2-ethoxy-4H-3,1-benzoxazin-4-one, m.p. 112°–114° C.; IR: 1760, 1630, 1590 cm$^{-1}$.

B.

In a similar manner, but starting with other appropriate compounds of Formula I in which an R′ is lower alkyl, the following compounds of Formula IF$_1$ are obtained:

5-bromoethyl-2-ethoxy-4H-3,1-benzoxazin-4-one;
6-bromomethyl-2-ethoxy-4H-3,1-benzoxazin-4-one;
7-bromomethyl-2-ethoxy-4H-3,1-benzoxazin-4-one;
8-bromomethyl-2-ethoxy-4H-3,1-benzoxazin-4-one;
5-(5-bromopentyl)-2-isobutoxy-4H-3,1-benzoxazin-4-one;
5-bromomethyl-2-(1-cyclopropylethyl)oxy-4H-3,1-benzoxazin-4-one;
7-(iodoethyl-2-imidazolyloxy-4H-3,1-benzoxazin-4-one;
7-amino-5-(3-chloropropyl)-2-benzyloxy-4H-3,1-benzoxazin-4-one; and
5-(2-bromobutyl)-2-ethoxy-4H-3,1-benzoxazin-4-one.

EXAMPLE VII

A. Preparation of 5-(Dibromomethyl)-2-ethoxy-4H,3,1-benzoxaxin-4-one and Related Compuunds of Formula IF$_2$ Proceeding in the same manner as Example VI, a solution of 2-ethoxy-5-methyl-4H,3,1-benzoxazin-4-one (2 gm), N-bromosuccinimide (4.05 gm) and AIBN (25 mg) in carbon tetrachloride was heated for 4 hours at reflux. The solvent was evaporated and the residue was purified by column chromatography (20% ethyl acetate:petroleum ether) to give 5-(dibromomethyl)-2-ethoxy-4H-3,1-benzoxazin-4-one, m.p. 98°–99° C; IR: 1750, 1640 cm$^{-1}$.

B.

In the same manner, but replacing the 2-ethoxy-5-methyl-4H-3,1-benzoxazin-4-one with other compounds of Formula I, the following compounds of Formula IF$_2$ are prepared:

6-dibromomethyl-2-ethoxy-4H-3,1-benzoxazin-4-one;
7-dibromomethyl-2-ethoxy-4H-3,1-benzoxazin-4-one;
8-dibromomethyl-2-ethoxy-4H-3,1-benzoxazin-4-one;
5-(5-dibromopentyl)-2-isobutoxy-4H-3,1-benzoxazin-4-one;
5-dibromomethyl-2-(1-cyclopropylethyl)oxy-4H-3,1-benzoxazin-4-one; and
5-(dibromobutyl)-2-ethoxy-4H-3,1-benzoxazin-4-one.

EXAMPLE VIII

A. Preparation of 2-Ethoxy-5-ethyl-4H,3,1-benzoxazin-4-one and Related Compounds of Formula IG$_1$ Methyl lithium (4.69 ml, 1.4M, Aldrich) was added to a suspension of cuprous iodide (0.62 gm) in anhydrous ether under argon at −78° C. The solution was stirred at −25° C. for 25 min. This solution was added to a solution of 2-ethoxy-5-bromomethyl-4H-3,1-benzoxazin-4-one (200 mg) in 15 ml anhydrous ether and 3 ml dry tetrahydrofuran at −60° C. Reaction was monitored by TLC until reaction completion. The reaction was quenched with saturated ammonium chloride solution and filtered. The filtrate was extracted in the usual manner. The ethereal layer was washed with water, dried over magnesium sulphate and evaporated to give an oil. The material was purified by thick layer chromatography ($R_f$=0.75, 3-% ethyl acetate: petroleum ether), to give 2-ethoxy-5-ethyl-4H-3,1-benzoxazin-4-one, m.p. 89°–91° C., H NMR: 1.3, 1.5 (2t, 6H, 2CH$_3$), 3.2 (q, 2H, CH$_2$), 4.5 (q, 2H, OC$\underline{H}_2$CH$_3$), 7.2 (m, 2H, ArH), 7.6 (t, 1H, ArH).

B.

Proceeding in the same manner, but replacing the lithium dimethyl cuprate, where desired, with other lithium dialkyl cuprates, and starting with other appropriate compounds of Formula IF$_1$, the following compounds of Formula IG$_1$ are prepared:

2-ethoxy-5-propyl-4H-3,1-benzoxazin-4-one;
2-ethoxy-5-butyl-4H-3,1-benzoxazin-4-one;
2-ethoxy-5-pentyl-4H-3,1-benzoxazin-4-one;
2-benzyloxy-5-methyl-4H-3,1-benzoxazin-4-one;
2-phenethyloxy-6-ethyl-4H-3,1-benzoxazin-4-one;
2-cyclopropyloxy-5-n-propyl-4H-3,1-benzoxazin-4-one; and
2-(1-cyclohexylethyl)oxy-5-ethyl-3,1-benzoxazin-4-one.

EXAMPLE IX

A. Preparation of 1-(2-Ethoxy-4H-3,1-benzoxazin-4-on-5-yl)-methyl-triphenylphosphonium bromide and Related Compounds of Formula IG$_2$ A solution of 5-bromomethyl-2-ethoxy-4H-3,1-benzoxazin-4-one (3.15 gm), prepared as described in Example VI above, and triphenylphosphine (5.44 gm) in toluene was heated at 60° C. for 6 hours. The insoluble precipitate was filtered, and the mother liquor was reduced to half of its original volume and refiltered, yielding 9 gm of 1-(2-ethoxy-4H-3,1-benzoxazin-4-on-5-yl)-methyl-triphenylphosphonium bromide, m.p. (turns yellow at) 125° C. IR: 1740, 1640 cm$^{-1}$;, decom. 135°–140° C.

B.

In a similar manner, but starting instead with other desired compounds of Formula IF$_1$, the preparation of which is described in Example VI, the following compounds of Formula IG$_2$ are prepared:

1-(2-ethoxy-4H-3,1-benzoxazin-4-on-5-yl)-ethyl-triphenylphosphonium bromide;
1-(2-ethoxy-4H-3,1-benzoxazin-4-on-6-yl)-methyl-triphenylphosphonium bromide;
1-(2-ethoxy-4H-3,1-benzoxazin-4-on-7-yl)-methyl-triphosphonium bromide;

1-(2-ethoxy-4H-3,1-benzoxazin-4-on-8-yl)-methyl-triphenylphosphonium bromide;

1-(2-ethoxy-4H-3,1-benzoxazin-4-on-5-yl)-butyl-triphenylphosphonium bromide;

1-(2-isopropoxy-7-nitro-4H-3,1-benzoxazin-4-on-5-yl)-ethyl-triphenylphosphonium bromide; and 1-[2-(4-methylcyclohexyl)oxy-4H-3,1-benzoxazin-4-on-6-yl]-methyl-triphenylphosphonium bromide.

EXAMPLE X

A. Preparation of (2-Ethoxy-1-propenyl)-4H-3,1-benzoxazin-4-one and Related Compounds of Formula IG$_3$ To a well-stirred suspension of (2-ethoxy-4H-3,1-benzoxazin-4-on-5-yl)methyltriphenylphosphonium bromide, prepared as described in Example IX, at −60° C. under argon, was added DBU (1-8-diazabicyclo[5,4,0]-undec-7-ene), 0.85 ml. After 30 min. at −40° C., 2 ml of acetaldehyde was added. The solution was stirred for 2 hours and warmed to room temperature. Solvent evaporation gave a residual oily solid which was chromatographed (silica gel 30% ethyl acetate:petroleum ether) to give the title compound, 2-ethoxy-5-(propenyl)-4H-3,1-benzoxazin-4-one, (R$_f$=0.77); IR: 1620, 1745 cm$^{-1}$.

B.

Proceeding in a similar manner, but replacing acetaldehyde with other alkylaldehydes, the following compounds of Formula IG$_3$ are prepared:

2-ethoxy-5-(1-butenyl)-4H-3,1-benzoxazin-4-one;
2-ethoxy-5-(1-hexenyl)-4H-3,1-benzoxazin-4-one;
2-ethoxy-5-(1-pentenyl)-4H-3,1-benzoxazin-4-one
2-methoxy-5-(1-butenyl)-4H-3,1-benzoxazin-4-one;
2-n-propoxy-5-(1-propenyl)-7-methylamino-4H-3,1-benzoxazin-4-one;
2-ethoxy-6-(1-butenyl)-4H-3,1-benzoxazin-4-one;
5-(1-hexenyl)-2-isopropoxy-7-nitro-4H-3,1-benzoxazin-4-one;
6-(1-butenyl)-2-(4-methylcyclohexyl)oxy-4H-3,1-benzoxazin-4-one;
2-n-butoxy-5-(isopropenyl)-7-methoxy-4H-3,1-benzoxazin-4-one;
2-s-butoxy-5-(isopentenyl)-4H-3,1-benzoxazin-4-one; and
2-n-octyloxy-(5-pentenyl)-7-nitro-4H-3,1-benzoxazin-4-one.

EXAMPLE XI

Compounds of Formula IH

A. Preparation of Methyl 4,5-dimethoxy-2-[4-(N-triphenylmethyl)-imidazolyl)-carbomethyloxy]amino-benzoate and Related compounds of Formula VI.

Trichloromethyl chloroformate (0.16 ml, 1.2 mmol.) was added to a solution of methyl 6,7-dimethoxyanthranilate (422 mg, 2 mmol.) in dry THF (30 ml) at room temperature under argon. After stirring for 90 minutes, anhydrous triethylamine (2 ml, 14.4 mmol.) and 4(N-triphenylmethyl)imidazolymethanol (749 mg, 2.2 mmol.) were added and the mixture was refluxed for one hour. The solvent was removed under reduced pressure. The residue was shaken with a mixture of ether/water (40 ml/40 ml) and the insoluble solid was collected by filtration to afford 936 mg (81%) of methyl 4,5-dimethoxy-2-[4-(N-triphenylmethyl)imidazolyl)carbomethyloxy]amino benzoate as a fine powder; m.p. 190°-192° C.; IR (KBr): $\nu_{max}$ 32670 cm$^{-1}$ (NH), 1730 cm$^{-1}$ (carbamate), 1690 (COOCH$_3$); H'NMR (CDCl$_3$): δ3.88 ppm (s, 6H, OCH$_3$), 5.13 ppm (s, 2H, OCH$_2$), 6.95–7.44 ppm (m, 18H, aromatic protons and imidazolyl C—H), 8.16 (s, 1H, imidazolyl C$_2$—H). 10.49 ppm (s, 1H, NH).

B.

In like manner, but starting instead with other appropriately substituted anthranilates, the following representative compounds of Formula VI are obtained:

methyl 6-methyl-2-[(4-(N-triphenylmethyl)imidazolyl)-carbomethyloxy]-amino benzoate;

methyl 6-ethyl-2-[(4-(N-triphenylmethyl)imidazolyl)-carbomethyloxy]-amino benzoate;

methyl 6-chloro-4-nitro-2-[(4-(N-triphenylmethyl)imidazolyl)carbomethyloxy]-amino benzoate;

methyl 6-ethylthio-4-bromomethyl-2-[(4-(N-triphenylmethyl)imidazolyl)carbomethyloxy]-amino benzoate;

methyl 4-amino-6-ethyl-2-[(4-(N-triphenylmethyl)imidazolyl)carbomethyloxy]-amino benzoate; and methyl 4-amino-6-ethyl-2-[(4-(N-triphenylmethyl)imidazolyl)carbomethyloxy]-amino benzoate.

C. Preparation of 6,7-Dimethoxy-2-(4-(N-triphenylmethyl)imidazolyl)-methyloxy-4H-3,1-benzoxazin-4-one and Related Compounds of Formula IH Methyl 4,5-dimethoxy-2-[(4-(N-triphenylmethyl)imidazolyl)carbomethyloxy]amino-benzoate (400 mg, 0.72 mmol.), prepared as described in Paragraph A of this Example, was stirred in a solution of 1N NaOH (10 ml), THF (20 ml), and methanol (20 ml) at room temperature for 3 hours. The organic solvent was removed under reduced pressure at 35° C. (bath temperature). The aqueous residue was diluted with water (15 ml) and acidified to pH 4 with 1N HCl. The white precipitate was collected by filtration to yield 73 mg (18%) of the expected product. The acidic filtrate was saturated with sodium chloride and extracted with ethyl acetate (2×20 ml). The combined ethyl acetate extract was dried (MgSO$_4$), evaporated to dryness. The residue was stirred in anhydrous ether (5 ml) and filtered to afford 173 mg (42%) of 4,5-dimethoxy-2-[(4-(N-triphenylmethyl)imidazolyl)carbomethyloxy]aminobenzoic acid. The combined yield of the expected acid was 246 mg (60%); mp. 200° C. (dec); IR (KBr): $\nu_{max}$ 3600–2800 cm$^{-1}$ (b, COOH), 1730 cm$^{-1}$ (carbamate), 1670 cm$^{-1}$ (COOH); H'NMR (DMSO—d$_6$): δ3.85 ppm (s, 6H, OCH$_2$), 6.85–7.65 ppm (m, 18H, aromatic protons and imidazolyl C$_5$—H), 7.90 (s, 1H, imidazolyl C$_2$—H), 11.07 ppm (b, 1H, NH).

1-(3-Dimethylaminopropyl)-3-ethylcarbodiimide hydrochloride (21 mg, 0.11 mmol.) was added in one portion to a suspension of the 4,5-dimethoxy-2-[(4-triphenylmethyl)imidazolyl)carbomethyloxy]aminobenzoic acid (49 mg, 0.09 mmol.) in anhydrous dichloromethane (2.5 ml) at room temperature under anhydrous conditions. After stirring for 30 minutes the clear reaction mixture was diluted with dichloromethane (17.5 ml) and washed with water (2×20 ml). The organic layer was dried with magnesium sulfate and evaporated to give a colorless syrup which was triturated with 50% pentane in anhydrous ether (3 ml) to give 35 mg (71%) of 6,7-dimethoxy-2-(4(N-triphenylmethyl)imidazolyl)-methyloxy-4H-3,1-benzoxazin-4-one as a white powder; m.p. 130°-133° C.; IR (KBr): $\nu_{max}$ 11760 cm$^{-1}$ (C=O), 1630 cm$^{-1}$ (C=N).

D.

In a similar manner, the following representative compounds of Formula IH are prepared from the corresponding amino-benzoates of Formula VI, the preparation of which is described in Paragrapghs A and B of this Example:

6-methyl-2-(4-(N-triphenylmethyl)imidazolyl)methyloxy-4H-3,1-benzoxazin-4-one;

6-ethyl-2-(4-(N-triphenylmethyl)imidazolyl)methyloxy-4H-3,1-benzoxazin-4-one;

6-ethylthio-4-bromomethyl-2-(4-(N-triphenylmethyl)imidazolyl)methyloxy-4H-3,1-benzoxazin-4-one; and 7-amino-5-ethyl-2-(4-(4-triphenylmethyl)imidazolyl)-methyloxy-4H-3,1-benzoxazin-4-one.

EXAMPLE XII

A. Preparation of 2-ethoxy-5-ethyl-7-nitro-H-3,1-benzoxazin-4-one and Related Compounds of Formula IA A solution of 2-carboethoxyamino-4-nitro-6-ethyl-benzoic acid and 1-(3-dimethylaminopropyl)-3-ethyl-carbodiimide hydrochloride in anhydrous THF(25 ml) was stirred at room temperature for 2½ hrs. The solution was evaporated by dryness and the residue partitioned between ethyl acetate and water. The ethyl acetate layer was dried over magnesium sulphate and evaporated to a solid. The solid was recrystallized from methylene chloride: petroleum ether to give the title compound, 2-ethoxy-5-ethyl-7-nitro-4H-3,1-benxozazin-4-one, m.p. 106°–107° C., Ir. 1770, 1660, 1600, 1595, 1535, 1515 cm$^{-1}$.

B.

In a similar manner, the following representative compounds of Formula IA are prepared from the corresponding amino-benzoic acids of Formula VII, the preparation of which is described in Preparation VI:

2-ethoxy-5-methyl-7-nitro-4H-3,1-benzoxazin-4-one;
2-benzyloxy-5-ethyl-7-nitro-4H-3,1-benzoxazin-4-one;
2-isopropyloxy-5-propyl-7-nitro-4H-3,1-benzoxazin-4-one;
2-isopropyloxy-5-butyl-4-nitro-4H-3,1-benzoxazin-4-one; and
2-cyclopropyloxy-5-iso-butyl-4-nitro-4H-3,1-benzoxazin-4-one.

EXAMPLE XIII

A. Preparation of 2-Ethoxy-5-methyl-7-methoxy-4H-3,1-benzoxazin-4-one and Related Compounds of Formula XF A solution of methyl 2-ethoxycarbonylamino-4-methoxy-6-methyl benzoate ester (100 mg), as prepared in Preparation XI, paragraph B, was stirred at room temperature in concentrated sulphuric acid (3 ml) for 2 hours. The solution was added dropwise to an ice-cold stirred mixture of ethyl acetate and saturated sodium bicarbonate solution. After neutralization, the mixture was extracted with ethyl acetate. The organic extract was dried over magnesium sulphate and evaporated to give a solid, 2-ethoxy-5-methyl-7-methoxy-4H-3,1-benzoxazin-4-one (60 mg), m.p. 138°–140° C.; anal. calcd. for $C_{12}H_{13}NO_4$: C, 61.27, H, 5.57, N, 5.95; found: C, 60.40, H, 5.63, N, 5.87, IR (KBr): 1760, 1650, 1610, 1570 cm$^{-1}$.

B.

Proceeding in a similar manner, but substituting other appropriate benzoates which may be prepared as described in Preparation XI, the following representative compounds of Formula XF are made:

2-ethoxy-5-ethyl-7-methoxy-4H-3,1-benzoxazin-4-one;
2-ethoxy-5-methyl-7-propoxy-4H-3,1-benzoxazin-4-one; and
2-isopropoxy-5-methyl-7-methoxy-4H-3,1-benzoxazin-4-one.

EXAMPLE XIV

A. Preparation of 2-isopropoxy-5-methyl-7-benzyloxy-4H-3,1-benzoxazin-4-one and Related Compounds of Formula XH A mixture of 2-(isopropoxy)carbonylamino-4-benzyloxy-6-methyl-benzoic acid (97 mg, 0.000282 mol) and 1-(3-dimethylaminopropyl)-3-ethyl-carbodiimide hydrochloride (EDCI) (200 mg) in methylene chloride (20 ml) was stirred at room temperature for 2 days. The solution was diluted with methylene chloride and extracted with water. The methylene chloride was further washed with brine solution, dried over sodium sulphate and evaporated to give a yellow solid. This material was further purified by column chromatography (5% ethyl acetate: pet. ether 30–60) to give 2-isopropoxy-5-methyl-7-benzyloxy-4H-3,1-benzoxazin-4-one (55 mg), m.p. 137°–138° C., IR (CHCl$_3$): 1755, 1640, 1605, 1569, 1460 cm$^{-1}$. H—NMR (CDCl$_3$): 1.4 (d, 6H, CH$_3$CHCH$_3$), 2.7 (s, 3H, CH$_3$), 5.15 (s, 2H, OCH$_2$Ph), 5.30 (p, 1H, CH), 6.8 (s, 1H, ArH), 7.40 (s, 5H, Ph).

B.

Proceeding in a similar manner, but replacing the 2-(isopropoxy)carbonylamino-4-benzyloxy-6-methyl-benzoic acid with other 6-substituted compounds of Formula XE, the following compounds of Formula XH are made:

2-isopropoxy-5-ethyl-7-benzyloxy-4H-3,1-benzoxazin-4-one;
2-isopropoxy-5-propyl-7-benzyloxy-4H-3,1-benzoxazin-4-one;
2-isopropoxy-5-isobutyl-7-benzyloxy-4H-3,1-benzoxazin-4-one;
2-ethoxy-5-ethyl-7-benzyloxy-4H-3,1-benzoxazin-4-one; and
2-ethoxy-5-methyl-7-benzyloxy-4H-3,1-benzoxazin-4-one.

EXAMPLE XV

A. Preparation of 5-Methyl-7-hydroxy-2-isopropoxy-4H-3,1-benzoxazin-4-one and Related Compounds of Formula X A solution of 5-methyl-7-benzyloxy-2-isopropoxy-4H-3,1-benzoxazin-4-one (50 mg) in ethyl acetate (80 ml) was hydrogenated over 10% palladium on charcoal at 50 psi hydrogen on a Parr hydrogenator for 5 hours. The catalyst was removed by suction filtration through Celite. The filtrate was evaporated to give a white solid which was further purified by thick layer chromatography (30% ethyl acetate: pet. ether 30–60) to give 5-methyl-7-hydroxy-2-isopropoxy-4H-3,1-benzoxazin-4-one as a white solid (23 mg), m.p. 258°–260° C. (decomp.), IR (KBr): 3100–3400, 1715, 1650, 1600 cm$^{-1}$. H—NMR (CDCl$_3$): 1.40 (d, 6H, CH$_3$CHCH$_3$), 2.40 (s, 3H, CH$_3$), 5.3 (p, 1H, CH), 6.7 (m, 2H, ArH).

B.

Proceeding in a similar manner, but replacing 5-methyl-7-benzyloxy-2-isopropoxy-4H-3,1-benzoxazin-4-one with other compounds of Formula XH, the following compounds of Formula X are made:

5-ethyl-7-hydroxy-2-isopropoxy-4H-3,1-benzoxazin-4-one;
5-ethyl-7-hydroxy-2-ethoxy-4H-3,1-benzoxazin-4-one;
5-methyl-7-hydroxy-2-ethoxy-4H-3,1-benzoxazin-4-one; and
5-isobutyl-7-hydroxy-2-isopropoxy-4H-3,1-benzoxazin-4-one.

EXAMPLE XVI

A. Preparation of 7-amino-2-ethoxy-5-ethyl-8-methyl-4H-3,1-benzoxazin-4-one and Related Compounds of Formula XI A solution of ethyl 4-amino-2-ethoxycarbonylamino-6-ethyl-3-methyl-benzoate (20 mg) in concentrated sulphuric acid (3 ml) was stirred at room temperature for 4 hrs. The solution was added dropwise to an ice-cold stirred mixture of ethyl acetate and saturated sodium bicarbonate solution. After neutralization, the mixture was extracted with ethyl acetate. The organic extract was dried over magnesium sulphate and evaporated to give a solid. This material is further purified by thick layer chromatography (25% ethyl acetate: pet,. ether 30–60) to yield 7-amino-2-ethoxy-5-ethyl-8-methyl-4H-3,1-benzoxazin-4-one (10 mg). IR (CHCl$_3$): 3500, 3420, 1740, 1650, 1610, 1565 cm$^{-1}$. H—NMR (CDCl$_3$): 1.20 (t, 3H, CH$_3$), 1.40 (t, 3H, CH$_3$), 2.20 (s, 3H, CH$_3$—Ar), 3.05 (q, 2H, CH$_2$Ar), 4.50 (q, 2H, CH$_2$O), 6.50 (s, 1H, ArH).

B.

Proceeding in a similar manner, but replacing 4-amino-2-ethoxycarbonylamino-6-ethyl-3-methyl-benzoate ester with other appropriate esters of Formula XIE, the following compounds of Formula XI are made:

7-amino-2-ethoxy-5,8-diethyl-4H-3,1-benzoxazin-4-one;
7-amino-2-ethoxy-5,8-dimethyl-4H-3,1-benzoxazin-4-one;
7-amino-2-ethoxy-5-propyl-8-methyl-4H-3,1-benzoxazin-4-one;
7-amino-2-ethoxy-5-isopropyl-8-methyl-4H-3,1-benzoxazin-4-one;
7-amino-2-ethoxy-5-isopropyl-8-methyl-4H-3,1-benzoxazin-4-one;
7-amino-2-isopropoxy-5-ethyl-8-methyl-4H-3,1-benzoxazin-4-one; and
7-amino-2-isopropoxy-5-isopropyl-8-methyl-4H-3,1-benzoxazin-4-one.

EXAMPLE XVII

Conversion of Free Base to Acid Addition Salt

A stoichiometric amount of 3% hydrogen chloride in dioxane is added to a solution of 1.0 g. of 7-amino-2-ethoxy-4H-3,1-benzoxazin-4-one in 20 ml dioxane. Diethyl ether is added until precipitation is complete. The product is filtered, washed with ether, air dried and recrystallized to give 7-amino-2-ethoxy-4H-3,1-benzoxazin-4-one hydrochloride.

In a similar manner, other compounds of Formula I in free base form may be converted to the acid addition salts by treatment with the appropriate acid, for example, hydrochloric acid, hydrobromic acid, sulfuric acid, nitric acid, phosphoric acid, acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

EXAMPLE XVIII

Conversion of Salt to Free Base 1.0 g of 7-amino-2-ethoxy-4H-3,1-benzoxazin-4-one HCl suspended in 50 ml of ether is stirred with a two-fold stoichiometric excess of dilute aqueous potassium carbonate solution until the salt is completely dissolved. The organic layer is then separated, washed twice with water, dried over magnesium sulfate and evaporated to yield 7-amino-2-ethoxy-5-methyl-4H-3,1-benzoxazin-4-one as the free base.

EXAMPLE XIX

Direct interchange of acid addition salts 7-amino-2-ethoxy-4H-3,1-benzoxazin-4-one acetate (1.0 g) is dissolved in 50 ml water containing a stoichiometric equivalent of sulfuric acid, and the solution evaporated to dryness. The product is suspended in ether and filtered, air dried and recrystallized from methanol/acetone to yield 2-ethoxy-5-ethyl-4H-3,1-benzoxazin-4-one sulfate.

In Examples XX through XXVII, the active ingredient is 5-methyl-7-hydroxy-2-isopropoxy-4H-3,1-benzoxazin-4-one. Other compounds of Formula I or Formula A and the pharmaceutically acceptable salts thereof may, of course, be substituted.

EXAMPLE XX

| Ingredients | Quantity per tablet, mgs. |
| --- | --- |
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE XXI

| Ingredients | Quantity per tablet, mgs. |
| --- | --- |
| Active ingredient | 100 |
| lactose, spray-dried | 148 |
| magnesium stearate | 2 |

The above ingredients are mixed and introduced into a hard-shell gelatin capsule.

EXAMPLE XXII

| Ingredients | Quantity per tablet, mgs. |
| --- | --- |
| Active ingredient | 200 |
| cornstarch | 50 |
| lactose | 145 |
| magnesium stearate | 5 |

The above ingredients are mixed intimately and pressed into single scored tablets.

EXAMPLE XXIII

| Ingredients | Quantity per tablet, mgs. |
|---|---|
| Active ingredient | 108 |
| lactose | 15 |
| cornstarch | 25 |
| magnesium stearate | 2 |

The above ingredients are mixed and introduced into a hard-shell gelatin capsule.

EXAMPLE XXIV

| Ingredients | Quantity per tablet, mgs. |
|---|---|
| Active ingredient | 150 |
| lactose | 92 |

The above ingredients are mixed and introduced into a hard-shell gelatin capsule.

EXAMPLE XXV

An injectable preparation buffered to a pH of 7 is prepared having the following composition:

| Ingredients | |
|---|---|
| Active ingredient | 0.2 g |
| $KH_2PO_4$ buffer (0.4 M solution) | 2 ml |
| KOH (1 N) | q.s. to pH 7 |
| water (distilled, sterile) | q.s. to 20 ml |

EXAMPLE XXVI

An oral suspension is prepared having the following composition:

| Ingredients | |
|---|---|
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

EXAMPLE XXVII

Topical Formulation

| Ingredients | grams |
|---|---|
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE XXVIII

Human Leukocyte Elastase Inhibition Assay

1. Enzyme

References: Barrett, A. J. (1981), *Methods in Enzymology*, 80C, 581-588.

Engelbrecht, et al., (1982), *Z. Physiol. Chem.*, 363, 305-315.

Fresh human leukocytes were obtained from a healthy donor, frozen and kept at −75° C. until use. Enzyme preparation followed the above referenced methods: cells were washed in saline, homogenized in the presence of 1M NaCl and 0.1% Brij 35 (Sigma Chemical C., No. P-1254). After centrifugation and concentration by dialysis against polyethylene glycol (MW 20,000), the material was chromatographed on Sephacryl S-300 (Pharmacia). Active fractions were combined, concentrated as before, and chromatographed on an affinity gel of bovine lung trypsin inhibitor attached to Sepharose CL-4B. Active fractions were combined, concentrated as before to approximately 0.3 micromolar in active elastase, and frozen in 1 ml aliquots at −75° C. until use.

2. Substrate 7-(Methoxysuccinyl-L-alanyl-L-alanyl-L-prolyl-L-valinamido)-4-methyl coumarin was obtained from Peninsula Laboratories, San Carlos, Calif., and 7-(methoxysuccinyl-L-alanyl-L-alanyl-L-prolyl-l-valinamido)-4-trifluoro-methyl coumarin was obtained from Enzyme Systems Products, Livermore, Calif. Stock solutions were made to 1 mM in dimethylsulfoxide.

3. Inhibitors

The compounds of Formula I to be assayed were dissolved in dimethylsulfoxide to give 5, 10, or 20 mM stock solutions, which may be further diluted as required.

4. Assay Buffer

The buffer consisted of 25 mM N-2-hydroxyethylpiperazine-N-2-ethane sulfonic acid, 1M sodium chloride, 0.1% w/v Brij 35, pH 7.8.

5. Procedure

A Perkin-Elmer Model 650-40 fluorescence spectrometer is set up as follows: ratio mode, full scale output 1 to 10 units, cell compartment thermostatted at 25° C. For the 4-methylcoumarin substrate, excitation and emission wavelengths are set to 370 and 460 nm, respectively, and for the 4-trifluoromethylcoumarin substrate to 400 and 505 nm. To 2.0 ml of assay buffer in a fluorescence cuvette is added 5 microliters substrate and 20 microliters enzyme, with mixing. The change in fluorescence is recorded on a strip chart recorder to measure the initial, uninhibited rate, typically 0.8 units per minute. After approximately two minutes of such recording, inhibitor (between 0.5 and 20 microliters of the stock solution) is added with mixing, and recording continued. The reaction is recorded until a new constant rate is achieved. This procedure is repeated for several (4-6) inhibitor concentrations. The data—a table of substrate concentration, inhibitor concentration, and observed reaction velocities—are fit to the appropriate equation by non-linear least squares multiple regression.

EXAMPLE XXIX

Human Thrombin Inhibition Assay

1. Enzyme

Human thrombin number T-8885 was obtained from Sigma Chemical Company, St. Louis, Mo., and reconstituted with water to approximately 2.5 NIH units/ml.

2. Substrate

BOC-L-Valyl-L-prolyl-L-arginyl-N-methyl-coumarinamide was obtained from Peninsula Laboratories, San Carlos, Calif. Solutions were made to 1 mM in dimethyl sulfoxide.

3. Inhibitors

As Example XXVIII.

4. Assay Buffer

The assay buffer consisted of 25 mM N-2-hydroxy ethylpiperazine-N-2-ethane sulfonic acid, 0.5M sodium chloride, 0.1% w/v polyethylene glycol 8000, pH 7.8.

Procedure

The procedure was as in Example XXVIII, except that 5 microliters of substrate and 2.5 microliters enzyme solution were used.

EXAMPLE XXX

Human Urokinase Inhibition Assay

1. Enzyme

Human Urokinase was obtained from Leo Laboratories, Pickering, Ontario, and made to approximately 2.5 mg/ml in 0.10M sodium citrate, 50 mM sodium chloride, pH 3.

2. Substrate

Glutaryl-glycyl-L-arginyl-methyl coumarin amide (Peninsula Laboratories, vide supra) was made to approximately 1 mM in 1:1 water:dimethylsulfoxide.

3. Inhibitors

As Example XXVIII.

4. Assay Buffer

The assay buffer consisted of 50 mM tris(hydroxymethyl)amino methane, 0.10M sodium chloride, 10 mM calcium chloride, pH 8.0.

5. Procedure

The procedure was as in Example XXVIII, with 5 microliters enzyme used.

EXAMPLE XXXI

Bovine Chymotrypsin Inhibition Assay

1. Enzyme

Chymotrypsin type II was obtained from Sigma Chemical Company and made to 0.25 mg/ml in 1 mM hydrochloric acid and kept at 4° C. until use.

2. Substrate 7-(Glutaryl-L-phenylalaninamido)-4-methyl coumarin was obtained from Sigma and made to 10 mM in 1:1 acetonitrile:dimethylsulfoxide.

3. Inhibitors

As Example XXVIII.

4. Assay Buffer

The assay buffer consisted of 25 mM N-2-hydroxy ethyl piperazine-N-2-ethane sulfonic acid, 0.1M potassium chloride, pH 7.8.

5. Procedure

As Example XXVIII.

EXAMPLE XXXII

Boar Acrosin Inhibition Assay

1. Enzyme

Boar acrosin was a gift of Professor W. Muller-Esterl, as purified in Muller-Esterl, et al., *Hoppe-Seyler's Z. Physiol. Chem.*, 361, 1811–1821, 1980, and was made to approximately 0.1 mg/ml in 1 mM HCl and kept at 4° C. until use.

2. Substrate 7-(N-benzoyl-L-argininamido)-4-methyl coumarin HCl was obtained from Sigma Chemical Company and made up to 2 mM in dimethyl sulfoxide.

3. Inhibitors

As Example XXVIII.

4. Assay Buffer

The assay buffer consisted of 0.10M N-2-hydroxy ethylpiperazine-N-2-ethane sulfonic acid, 50 mM calcium chloride, 0.01% v/v Triton X-100, pH 7.8.

5. Procedure

The procedure was as Example XXVIII, with 5 microliters substrate and 2.5 to 15 microliters enzyme as required to obtain approximately 0.5 fluorescent unit/minute uninhibited rate.

EXAMPLE XXXIII

Assay for Stability of Compounds in Whole Plasma

Whole, citrated human plasma was obtained from a local blook bank and kept frozen at −70° C. until use. Benzoxazinone (from a stock solution in dimethylsulfoxide) was added to plasma at 37° C. to a final concentration of 25 to 10 micromolar, and incubation was continued at 37°. At various times thereafter, aliquots were withdrawn and diluted 1:1 with acetonitrile, mixed on a vortex stirrer, centrifuged, and filtered through a 0.45 micron filter. Ten microliters of the filtrate was assayed by high pressure liquid chromatography on a C-18 reverse phase column, with ultraviolet detection. Retention times and concentrations were determined by comparison to standards. The integrated areas of the benzoxazinone peaks vs. incubation time were fit by non-linear least squares regression to a first-order exponential to obtain the half-time in plasma.

EXAMPLE XXXIV

Assay for Inhibition of Endothelial Cell Basement Membrane Degradation

Principle

Various serine proteases, including elastase, are secreted by murine activated macrophages, and cause the degradation of endothelial cell basement membrane. This assay tests the inhibitory potency of a test compound to as a measure of its ability to inhibit enzyme induced degradation of the endothelial cell basement membrane.

Methods

LE II murine lung capillary endothelial cells were grown to confluence in 24 well cluster dishes. Cells were lageled with 10 $\mu$Ci [$^{35}$S]-methionine per well, in medium deficient in methionine and supplemented with 10% fetal calf serum and 10 $\mu$g/ml ascorbate for two days.

Biosynthetically labeled basement membranes were prepared by lysing the cells with 0.5% Nonidet P40 for 5 minutes at room temperature and removing cytoskeletal degris with 0.25N NH$_4$OH, followed by several washes with phosphate buffer.

Activate murine macrophages were obtained by peritoneal lavage of female C3H/He mice injected intraperitoneally with *Corynebacterium parvum* 7 days prior to the experiment.

Macrophages were either layere on the basement membrane (5×10⁵ cells/well) or used to prepare conditioned medium in separate dishes that were then incubated with the basement membrane.

Test compound was dissolved in DMSO at $10^{-2}$M–$10^{-3}$M, diluted with medium containing 1 mg/ml bovine serum albumin, and tested at $10^{-5}$M.

Macrophages, conditioned medium, or 5 μ/ml porcine pancreatic elastase (Sigma) were incubated with the basement membrane at 37° C. for 4 hours in the presence or absence of test compound. Aliquots of the medium were counted for ³H and ³⁵S in a liquid scintillation counter.

Results may be expressed as % inhibition of the release of radioactivity after correction for spontaneous release of radioactivity determined in control wells. Compounds of Formula I which were tested in this assay exhibited significant inhibitory potency against degredation of the basement membrane.

What we claim is:

1. A compound of the formula:

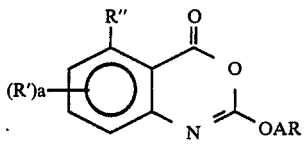

wherein:
a is an integer of 0 to 3;
A is a bond, or alkylene having one to eight carbon atoms;
R is hydrogen, imidazolyl, phenyl, or cycloalkyl having three to six carbon atoms, wherein the phenyl, imidazolyl or cycloalkyl ring is optionally substituted with 1 to 3 substituents independently selected from the group consisting of lower alkyl having one to four carbon atoms, lower alkoxy having one to four carbon atoms, —N(R¹)₂, —NO₂, halo, and lower alkylthio having one to four carbon atoms; and
each R' and R" are independently selected from the group consisting of hydroxy, benzyloxy, lower alkyl having one to six carbon atoms, lower alkenyl having two to six carbon atoms, halo, lower alkoxy having one to six carbon atoms, halo-lower alkyl having one to six carbon atoms, lower alkylthio having one to six carbon atoms, —NO₂, —N(R¹)₂, —NR¹CO₂R², —NR¹C(O)R², and —NR¹C(O)N(R¹)₂,
in which
each R¹ is independently hydrogen or lower alkyl having one to six carbon atoms, or together form a piperidine or piperazine ring optionally substituted at the ring nitrogen with lower alkyl having one to four carbon atoms, or —CH₂CH₂OH;
each R² is independently lower alkyl having one to four carbon atoms, and
A is alkylene if R is hydrogen,
or a pharmaceutically acceptable acid addition salt thereof.

2. A compound of claim 1 in which R is hydrogen, phenyl, or benzyl and A is alkylene having one to four carbon atoms.

3. A compound of claim 2 in which A is isopropylene, methylene, or ethylene.

4. A compound of claim 3 in which R" is lower alkyl having one to six carbon atoms or lower alkenyl having two to six carbon atoms.

5. A compound of claim 4 in which R" is lower alkyl having one to three carbon atoms.

6. A compound of claim 5 in which a is one and R' is in the 7-position.

7. A compound of claim 6 in which R' is selected from the group consisting of hydroxy, benzyloxy, and lower alkoxy having one to six carbon atoms.

8. A compound of claim 7 in which A is isopropylene, R is hydrogen and R' is hydroxy.

9. A compound of claim 8 in which R" is methyl, namely 7-hydroxy-2-isopropoxy-5-methyl-4H-3,1-benzoxazin-4-one.

10. A compound of claim 8 in which R" is ethyl, namely 5-ethyl-7-hydroxy-2-isopropoxy-4H-3,1-benzoxazin-4-one.

11. A compound of claim 8 in which R" is isopropyl, namely 2-isopropoxy-5-isopropyl-7-hydroxy-4H-3,1-benzoxazin-4-one.

12. A compound of claim 7 in which A is ethylene, R is hydrogen, and R' is hydroxy.

13. A compound of claim 12 in which R" is methyl, namely 2-ethoxy-5-methyl-7-hydroxy-4H-3,1-benzoxazin-4-one.

14. A compound of claim 7 in which A is isopropylene, R is hydrogen, and R' is benzyloxy.

15. A compound of claim 14 in which R" is methyl, namely 7-benzyloxy-2-isoporpoxy-5-methyl-4H-3,1-benzoxazin-4-one.

16. A compound of claim 14 in which R" is ethyl, namely 7-benzyloxy-5-ethyl-2-isopropoxy-4H-3,1-benzoxazin-4-one.

17. A compound of claim 14 in which R" is isopropyl, namely 7-benzyloxy-2-isopropoxy-5-isopropyl- 4H-3,1-benzoxazin-4-one.

18. A compound of claim 7 in which A is ethylene, R is hydrogen, and R' is benzyloxy.

19. A compound of claim 18 in which R" is methyl, namely 7-benzyloxy-2-ethoxy-5-methyl-4H-3,1-benzoxazin-4-one.

20. A compound of claim 5 in which a is two, and a first R' is in the 7-position and a second R' is in the 8-position.

21. A compound of claim 20 in which the first R' is selected from the group consisting of —NO₂ and —NH₂ and the second R' is selected from the group consisting of lower alkyl, lower alkenyl and lower alkoxy.

22. A compound of claim 21 in which R is hydrogen and the first R' is —NO₂.

23. A compound of claim 22 in which A is ethylene, R" is ethyl and the second R' is ethyl, namely 2-ethoxy-5,8-diethyl-7-nitro-4H-3,1-benzoxazin-4-one.

24. A compound of claim 22 in which A is isopropylene, R" is methyl, and the second R' is methyl, namely 2-isopropoxy-5,8-dimethyl-7-nitro-4H-3,1-benzoxazin-4-one.

25. A compound of claim 21 in which R is hydrogen and the first R' is —NH₂.

26. A compound of claim 25 in which A is ethylene, R" is methyl, and the second R' is isopropyl, namely 2-ethoxy-8-isopropyl-5-methyl-7-nitro-4H-31,1-benzoxazin-4-one.

27. A compound of claim 25 in which A is ethylene, R" is ethyl, and the second R' is ethyl, namely 7-amino-2-ethoxy-5,8-diethyl-4H-3,1-benzoxazin-4-one.

28. A compound of claim 25 in which A is ethylene, R" is methyl, and the second R' is methyl, namely 7-amino-2-ethoxy-5,8-dimethyl-4H-3,1-benzoxazin-4-one.

29. A compound of claim 25 in which A is ethylene, R" is methyl, and the second R' is isopropyl, namely 7-amino-2-ethoxy-8-isopropyl-5-methyl-4H-3,1-benzoxazin-4-one.

30. A compound of the formula:

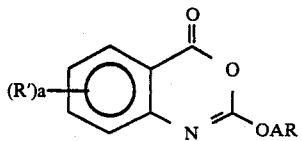

wherein:
a is an integer of 1 to 4;
A is alkylene having one to eight carbon atoms;
R is hydrogen; and
at least one R' represents a substituent at one of the 5- and 7-positions, and each R' is independently selected from the group consisting of hydroxy, benzyloxy, lower alkyl having one to six carbon atoms, lower alkenyl having two to six carbon atoms, halo-lower alkyl having one to six carbon atoms, lower alkylthio having one to six carbon atoms, halo, $-NO_2$, $-N(R^1)_2$, $-NR^1CO_2R^2$, $-NR^1COR^2$, and $-NR^1C(O)N(R^1)_2$,
in which
each $R^1$ is independently hydrogen or lower alkyl having one to four carbon atoms, or together form a piperidine or piperazine ring optionally substituted at the ring nitrogen by lower alkyl having one to four carbon atoms or $-CH_2CH_2OH$, and
each $R^2$ is independently lower alkyl having one to four carbons atoms, or a pharmaceutically acceptable acid addition salt thereof.

31. A compound of claim 30 in which a is 1 and R' is in the 7-position and selected from the group consisting of hydroxy, benzyloxy, or lower alkoxy having one to six carbon atoms.

32. A compound of claim 31 in which A is isopropylene, R is hydrogen, and R' hydroxy, namely 7-hydroxy-2-isopropoxy-4H-3,1-benzoxazin-4-one.

33. A method of inhibiting serine proteases in humans and animals which method comprises administering to a human or animal in need of such treatment a compound of the formula:

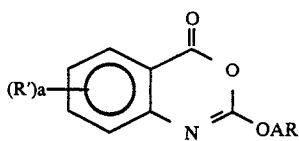

wherein:
a is an integer of 1 to 4;
A is a bond, or alkylene having one to eight carbon atoms;
R is hydrogen, phenyl, imidazolyl or cycloalkyl having three to six carbon atoms, wherein the phenyl, imidazolyl or cycloalkyl ring is optionally substituted with 1 to 3 substituents independently selected from the group consisting of lower alkyl having one to four carbon atoms, lower alkoxy having one to four carbon atoms, $-N(R^1)_2$, $-NO_2$, halo or lower alkylthio having one to four carbon atoms, and,
at least one R' represents a substituent at one of the 5- and 7-positions, and each R' is independently selected from the group consisting of hydroxy, benzyloxy, lower alkyl having one to six atoms, lower alkenyl having two to six carbon atoms, lower alkoxy having one to six carbon atoms, lower alkylthio or halo-lower alkyl having one to six carbon atoms, halo, $-NO_2$, $-N(R^1)_2$, $-NR^1CO_2R^2$, $-NR^1COR^2$, and $-NR^1C(O)N(R^1)_2$, in which each $R^1$ is independently hydrogen or lower alkyl having one to four carbon atoms, or together form a piperidine or a piperazine ring optionally substituted at the ring nitrogen by lower alkyl having one to four carbon atoms or $-CH_2CH_2OH$;
each $R^2$ is independently lower alkyl having one to four carbon atoms,
A is an alkylene group if R is hydrogen,
or a pharmaceutically acceptable acid addition salt thereof.

34. The method of claim 33 in which the serine protease is human leukocyte elastase.

35. The method of claim 33 in which the serine protease is trypsin.

36. A pharmaceutical composition which comprises a therapeutically effective amount of a compound of the formula:

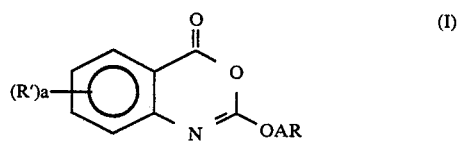

wherein:
a is an integer of 1 to 4;
A is a bond, or alkylene having one to eight carbon atoms;
R is hydrogen, phenyl, imidazolyl or cycloalkyl having three to six carbon atoms, wherein the phenyl, imidazolyl or cycloalkyl ring is optionally substituted with 1 to 3 substituents independently selected from the group consisting of lower alkyl having one to four carbon atoms, lower alkoxy having one to four carbon atoms, $-N(R^1)_2$, $-NO_2$, halo or lower alkylthio having one to four carbon atoms, and,
at least one R' represents a substituent at one of the 5- and 7-positions, and each R' is independently selected from the group consisting of hydroxy, benzyloxy, lower alkyl having one to six atoms, lower alkenyl having two to six carbon atoms, lower alkoxy having one to six carbon atoms, lower alkylthio or halo-lower alkyl having one to six carbon atoms, halo, $-NO_2$, $-N(R^1)_2$, $-NR^1CO_2R^2$, $-NR^1COR^2$, and $-NR^1C(O)N(R^1)_2$,
in which
each $R^1$ is independently hydrogen or lower alkyl having one to four carbon atoms, or together form a piperidine or a piperazine ring optionally substituted at the ring nitrogen by lower alkyl having one to four carbon atoms or $-CH_2CH_2OH$;
each $R^2$ is independently lower alkyl having one to four carbon atoms,
A is an alkylene group if R is hydrogen,,
or a pharmaceutically acceptable acid addition salt thereof, in admixture with at least one pharmaceutically acceptable excipient.

37. A pharmaceutical composition which comprises a therapeutically effective amount of a compound of claim 1, or a pharmaceutically acceptable acid addition salt thereof, in admixture with at least one pharmaceutically acceptable excipient.

38. A pharmaceutical composition which comprises a therapeutically effective amount of a compound of claim 30, or a pharmaceutically acceptable acid addition salt thereof, in admixture with at least one pharmaceutically acceptable excipient.

* * * * *